US011234890B2

(12) United States Patent
    Ahn et al.

(10) Patent No.: US 11,234,890 B2
(45) Date of Patent: Feb. 1, 2022

(54) METHOD AND APPARATUS FOR RECOGNIZING GAIT TASK

(71) Applicant: Samsung Electronics Co., Ltd., Suwon-si, Gyeonggi-do (KR)

(72) Inventors: Sunghwan Ahn, Seoul (KR); Youngbo Shim, Seoul (KR); Seungyong Hyung, Yongin-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 1081 days.

(21) Appl. No.: 14/850,288

(22) Filed: Sep. 10, 2015

(65) Prior Publication Data

US 2016/0074272 A1    Mar. 17, 2016

(30) Foreign Application Priority Data

Sep. 12, 2014    (KR) .................. 10-2014-0121026

(51) Int. Cl.
    *A61H 3/00* (2006.01)
    *A61B 5/11* (2006.01)
    *A61B 5/00* (2006.01)

(52) U.S. Cl.
    CPC ............... *A61H 3/00* (2013.01); *A61B 5/112* (2013.01); *A61B 5/1122* (2013.01); *A61B 5/1123* (2013.01); *A61B 5/4851* (2013.01); *A61B 5/7264* (2013.01); *A61B 5/7267* (2013.01); *A61H 2003/001* (2013.01); *A61H 2201/5012* (2013.01); *A61H 2230/605* (2013.01)

(58) Field of Classification Search
    CPC ..... A61B 5/112; A61B 5/7264; A61B 5/4851;
    A61B 5/1123; A61B 5/7267; A61B 5/1122; A61H 3/00; A61H 2003/001; A61H 2230/605; A61H 2201/5012; A61F 2005/0155
    See application file for complete search history.

(56) References Cited

U.S. PATENT DOCUMENTS 9,149,222 B1 * 10/2015 Zets .................. A61B 5/16
2009/0265018 A1    10/2009 Goldfarb et al.
(Continued)

FOREIGN PATENT DOCUMENTS

CN    101388080 A    3/2009
CN    102119877 A    7/2011
(Continued)

OTHER PUBLICATIONS

Cao-yuan Zhao et al., "The Application of Machine-Learning on Lower Limb Motion Analysis in Human Exoskeleton System", Oct. 29, 2012, Social Robotics, Springer Berlin Heidelberg, Berlin, Heidelberg, pp. 600-611.
(Continued)

*Primary Examiner* — Nyca T Nguyen
(74) *Attorney, Agent, or Firm* — Harness, Dickey & Pierce, P.L.C.

(57) ABSTRACT

Methods and apparatuses for recognizing a gait task, that may detect a gait pattern of a user based on sensed data, generate a gait feature of the gait pattern based on similarities between the gait pattern and similar gait data extracted from each of a plurality of databases, and estimate a gait task corresponding to the gait pattern by applying the gait feature to a desired learning model, may be provided.

28 Claims, 19 Drawing Sheets

(56) References Cited

U.S. PATENT DOCUMENTS

| | | |
|---|---|---|
| 2009/0319054 A1 | 12/2009 | Sankai |
| 2010/0271051 A1* | 10/2010 | Sankai ............... A61H 1/0262 324/679 |
| 2011/0112443 A1* | 5/2011 | Williams ............. A61B 5/112 600/595 |
| 2012/0089330 A1* | 4/2012 | Hesch ................. G01C 21/16 701/433 |
| 2012/0215140 A1 | 8/2012 | Hirata et al. |
| 2014/0094345 A1* | 4/2014 | Kim .................. A63B 21/4009 482/7 |
| 2014/0303508 A1* | 10/2014 | Plotnik-Peleg ........ A61B 5/744 600/483 |
| 2016/0007885 A1* | 1/2016 | Basta ................. A61B 5/222 482/5 |

FOREIGN PATENT DOCUMENTS

| | | |
|---|---|---|
| CN | 103431929 A | 12/2013 |
| JP | 2005-211086 A | 8/2005 |
| JP | 2010-017465 A | 1/2010 |
| JP | 2010-263934 A | 11/2010 |
| JP | 2011-019669 A | 2/2011 |
| KR | 100957985 B1 | 5/2010 |
| KR | 10-2011-0120626 A | 11/2011 |
| KR | 101082161 B1 | 11/2011 |
| KR | 10-2013-0010609 A | 1/2013 |
| KR | 1020130001663 A | 1/2013 |
| KR | 101340085 B1 | 12/2013 |
| KR | 1020140013335 A | 2/2014 |
| KR | 10-1422669 B1 | 7/2014 |
| KR | 1020150053854 A | 5/2015 |
| KR | 1020150085212 A | 7/2015 |

OTHER PUBLICATIONS

European Search Report dated Feb. 16, 2016 in corresponding European Application No. 15179279.3.

Chinese Office Action dated Dec. 3, 2018 issued in Chinese Application No. 201510579072.0 (English translation provided).

Huseyin Atakan Varol, et al. "Multiclass Real-Time Intent Recognition of a Powered Lower Limb Prosthesis," IEEE Transaction on Biomedical Engineering, vol. 57, No. 3 pp. 542-551 (2010).

* cited by examiner

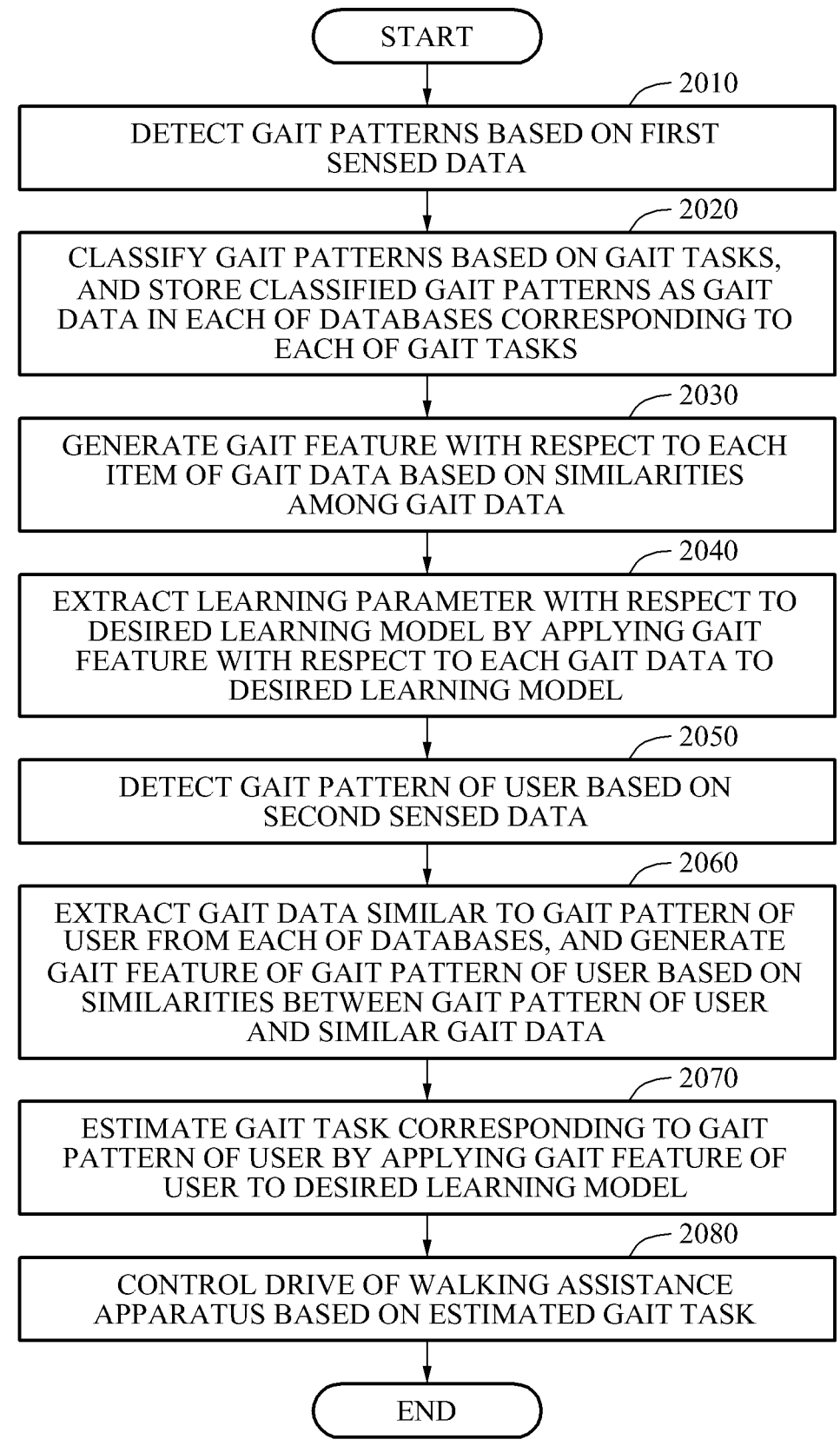

METHOD AND APPARATUS FOR RECOGNIZING GAIT TASK

CROSS-REFERENCE TO RELATED APPLICATION

This application claims priority under 35 U.S.C. § 119 to Korean Patent Application No. 10-2014-0121026, filed on Sep. 12, 2014, in the Korean Intellectual Property Office, the entire contents of which are incorporated herein by reference in its entirety.

BACKGROUND

1. Field

Example embodiments relate to methods and/or apparatuses for recognizing a gait task.

2. Description of the Related Art

With the onset of rapidly aging societies, many people are experiencing inconvenience and/or pain from joint problems. Thus, there is a growing interest in motion assistance apparatuses that enable the elderly and/or patients having joint problems to walk with less effort. Furthermore, motion assistance apparatuses for intensifying muscular strength of human bodies may be useful for military purposes.

In general, motion assistance apparatuses for assisting motion of lower parts of bodies may include body frames disposed on trunks of users, pelvic frames coupled to lower sides of the body frames to cover pelvises of the users, femoral frames disposed on thighs of the users, sural frames disposed on calves of the users, and/or pedial frames disposed on feet of the users. The pelvic frames and femoral frames may be connected rotatably by hip joint portions, the femoral frames and sural frames may be connected rotatably by knee joint portions, and/or the sural frames and pedial frames may be connected rotatably by ankle joint portions.

Recently, research for improving the usability of motion assistance apparatuses is being carried out.

SUMMARY

At least one example embodiment relates to an apparatus for recognizing a gait task.

According to an example embodiment, an apparatus for recognizing a gait task includes a gait pattern detector configured to detect a gait pattern of a user based on sensed data, a gait feature generator configured to extract gait data similar to the detected gait pattern from each of a plurality of databases corresponding to each of a plurality of gait tasks, and generate a gait feature of the gait pattern based on similarities between the gait pattern and the similar gait data, a gait task estimator configured to estimate a gait task corresponding to the gait pattern by applying the gait feature to a set learning model, and a drive controller configured to drive a walking assistance apparatus based on the estimated gait task.

In some example embodiments, the gait pattern detector may be configured to sense a heal strike indicating a state in which a sole of the user touches a ground from the sensed data, and detect the gait pattern based on a basic unit of one of a step including a single heel strike and a stride including two steps.

In some example embodiments, the sensed data may include at least one of acceleration data sensed by an inertial measurement unit (IMU) sensor, angular velocity data sensed by the IMU sensor, joint angle data sensed by a potentiometer, joint angular velocity data sensed by the potentiometer, and electromyography (EMG) data extracted from an EMG sensor.

In some example embodiments, the gait pattern detector may include a normalizer configured to normalize the gait pattern with respect to at least one of a time axis and a data axis.

In some example embodiments, the gait feature generator may be configured to calculate the similarities between the gait pattern and gait data included in each of the plurality of databases, and extract the similar gait data from the each of the plurality of databases based on the calculated similarities.

In some example embodiments, the gait feature generator may be configured to calculate a mean value of the similarities between the gait pattern and the similar gait data, and generate a gait feature vector including a feature value corresponding to each of the plurality of gait tasks based on the mean value as an element.

In some example embodiments, the gait feature generator may be configured to generate the gait feature by normalizing the gait feature vector.

In some example embodiments, the gait feature generator may be configured to calculate the similarities between the gait pattern and the gait data or the similarities between the gait pattern and the similar gait data using at least one of an L1 norm, an L2 norm, a normalized cross correlation (NCC), and dynamic time warping (DTW).

In some example embodiments, the gait task estimator may be configured to input the gait feature into the set learning model, and estimate the gait task corresponding to the gait pattern by applying a set learning parameter to the set learning model.

In some example embodiments, the set learning parameter may be extracted from gait data included in each of the plurality of databases based on the set learning model.

In some example embodiments, the gait task estimator may be configured to obtain the set learning parameter from an external device using a communication interface.

In some example embodiments, the gait task estimator may be configured to map the gait feature to a feature space of a set dimension, and input the mapped gait feature into the set learning model.

According to another example embodiment, a preprocessing apparatus for gait task recognition includes a gait pattern detector configured to detect a plurality of gait patterns based on sensed data, a database constructor configured to classify the plurality of gait patterns based on a plurality of gait tasks, and store the classified plurality of gait patterns as gait data in each of a plurality of databases corresponding to each of the plurality of gait tasks, a gait feature generator configured to generate a gait feature with respect to each of the gait data based on similarities among the gait data, and a learning parameter extractor configured to extract a learning parameter with respect to a set learning model by applying the gait feature with respect to the each of the gait data to the set learning model.

In some example embodiments, the gait pattern detector may be configured to sense a heal strike indicating a state in which a sole of a user touches a ground from the sensed data, and detect the gait pattern based on a basic unit of a step including a single heel strike or a stride including two steps.

In some example embodiments, the sensed data may include at least one of acceleration data sensed by an IMU sensor, angular velocity data sensed by the IMU sensor, joint angle data sensed by a potentiometer, joint angular velocity data sensed by the potentiometer, and EMG data extracted from an EMG sensor.

In some example embodiments, the gait pattern detector may include a normalizer configured to normalize the plurality of gait patterns with respect to at least one of a time axis and a data axis.

In some example embodiments, the data constructor may be configured to store the classified plurality of gait patterns as the gait data in each of the plurality of databases using a k-d tree structure.

In some example embodiments, the gait feature generator may be configured to extract gait data similar to each of the gait data from each of the plurality of databases, and generate the gait feature of the each of the gait data based on the similarities between the each of the gait data and gait data similar thereto.

In some example embodiments, the gait feature generator may be configured to calculate a mean value of the similarities between the each of the gait data and the similar gait data, and generate a gait feature vector including a feature value corresponding to each of the plurality of gait tasks based on the mean value as an element.

In some example embodiments, the gait feature generator may be configured to generate the gait feature by normalizing the gait feature vector with respect to each of the gait data.

In some example embodiments, the learning parameter extractor may be configured to map the gait feature with respect to each of the gait data to a feature space of a set dimension, and input the mapped gait feature into the set learning model.

In some example embodiments, the learning parameter extractor may be configured to transmit the extracted learning parameter to an external device using a communication interface.

According to still another example embodiment, an apparatus for recognizing a gait task includes a gait pattern detector configured to detect a plurality of gait patterns based on first sensed data, a database constructor configured to classify the plurality of gait patterns based on a plurality of gait tasks, and store the classified plurality of gait patterns as gait data in each of a plurality of databases corresponding to each of the plurality of gait tasks, a gait feature generator configured to generate a gait feature with respect to each of the gait data based on similarities among the gait data, a learning parameter extractor configured to extract a learning parameter with respect to a set learning model by applying the gait feature with respect to the each of the gait data to the set learning model, a user gait pattern detector configured to detect a gait pattern of a user based on second sensed data, a user gait feature generator configured to extract gait data similar to the gait pattern of the user from each of the plurality of databases, and generate a gait feature of the gait pattern of the user based on similarities between the gait pattern of the user and the similar gait data, a gait task estimator configured to estimate a gait task corresponding to the gait pattern of the user by applying the gait feature of the gait pattern of the user to the set learning model, and a drive controller configured to drive a walking assistance apparatus based on the estimated gait task.

At least one example embodiment relates to a method of recognizing a gait task.

According to an example embodiment, a method of recognizing a gait task includes detecting a gait pattern of a user based on sensed data, extracting gait data similar to the detected gait pattern from each of a plurality of databases corresponding to each of a plurality of gait tasks, and generating a gait feature of the gait pattern based on similarities between the gait pattern and the similar gait data, estimating a gait task corresponding to the gait pattern by applying the gait feature to a set learning model, and controlling a drive of a walking assistance apparatus based on the estimated gait task.

According to another example embodiment, a preprocessing method for gait task recognition including detecting a plurality of gait patterns based on sensed data, classifying the plurality of gait patterns based on a plurality of gait tasks, and storing the classified plurality of gait patterns as gait data in each of a plurality of databases corresponding to each of the plurality of gait tasks, generating a gait feature with respect to each of the gait data based on similarities among the gait data, and extracting a learning parameter with respect to a set learning model by applying the gait feature with respect to each of the gait data to the set learning model.

According to still another example embodiment, a method of recognizing a gait task includes detecting a plurality of gait patterns based on first sensed data, classifying the plurality of gait patterns based on a plurality of gait tasks, and storing the classified plurality of gait patterns as gait data in each of a plurality of databases corresponding to each of the plurality of gait tasks, generating a gait feature with respect to each of the gait data based on similarities among the gait data, extracting a learning parameter with respect to a set learning model by applying the gait feature with respect to the each of the gait data to the set learning model, detecting a gait pattern of a user based on second sensed data, extracting gait data similar to the gait pattern of the user from each of the plurality of databases, and generating a gait feature of the gait pattern of the user based on similarities between the gait pattern of the user and the similar gait data, estimating a gait task corresponding to the gait pattern of the user by applying the gait feature of the gait pattern of the user to the set learning model, and controlling a drive of a walking assistance apparatus based on the estimated gait task.

According to still another example embodiment, an apparatus for adaptively recognizing a gait task includes a gait pattern detector configured to detect a gait pattern based on first sensed data, a gait feature generator configured to search a plurality of databases corresponding a plurality of gait tasks, respectively, and generate a gait feature corresponding the detected gait pattern based on the search, a gait task estimator configured to estimate a gait task corresponding to the detected gait pattern by applying the gait feature to a set learning model, and a drive controller configured to drive a walking assistance apparatus based on the estimated gait task.

In some example embodiments, the gait feature generator may be configured to search the plurality of databases for gait data similar to the detected gait pattern.

In some example embodiments, the gait feature generator may be configured to generate the gait feature corresponding to the detected gait pattern based on similarities between the detected gait pattern and the similar gait data.

In some example embodiments, the gait task estimator may be configured to estimate the gait task corresponding to the detected gait pattern by inputting the gait feature into the set learning model, and apply a set learning parameter, which is extracted by applying the gait feature corresponding to the detected gait pattern, to the set learning model.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects of example embodiments will become apparent and more readily appreciated from the following description of some example embodiments, taken in conjunction with the accompanying drawings of which:

FIG. 20 is a flowchart illustrating a method of recognizing a gait task according to an example embodiment.

DETAILED DESCRIPTION

Figure 1A:
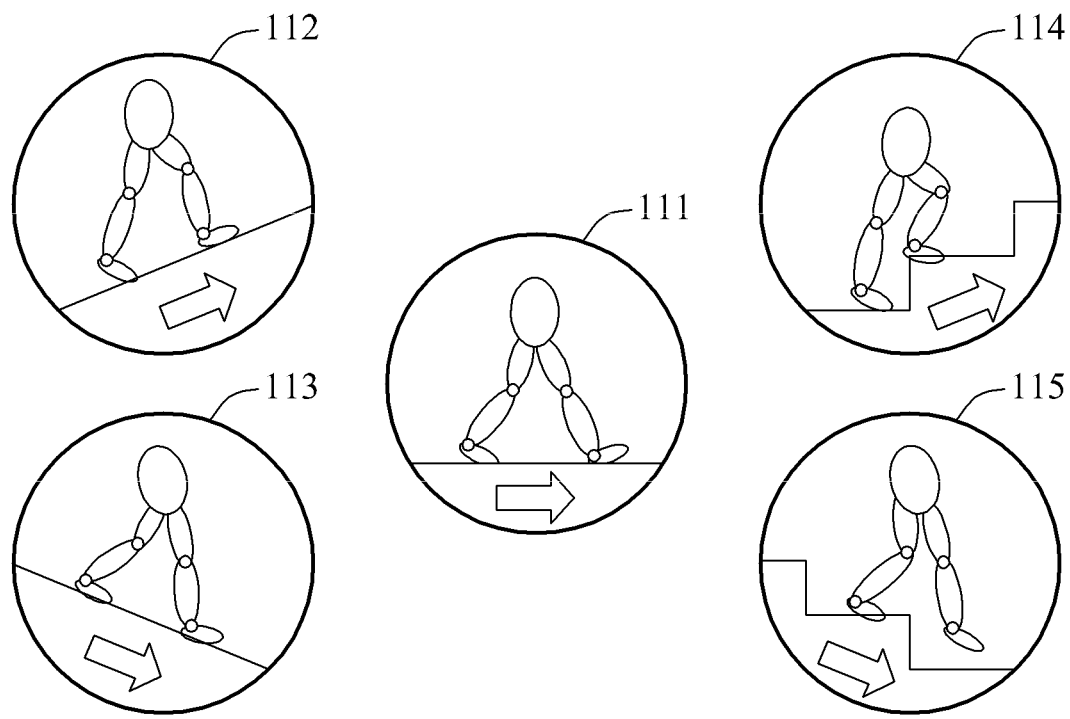
FIGS. 1A and 1B illustrate gait tasks according to an example embodiment.

Various example embodiments will now be described more fully with reference to the accompanying drawings in which some example embodiments are shown. Like reference numerals refer to like elements throughout. In the drawings, the thicknesses of layers and regions are exaggerated for clarity.

Detailed illustrative example embodiments are disclosed herein. However, specific structural and functional details disclosed herein are merely representative for purposes of describing example embodiments. Example embodiments may be embodied in many alternate forms and should not be construed as limited to only those set forth herein.

It should be understood, however, that there is no intent to limit this disclosure to the particular example embodiments disclosed. On the contrary, example embodiments are to cover all modifications, equivalents, and alternatives falling within the scope of the example embodiments.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of this disclosure. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular example embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which example embodiments belong. It will be further understood that terms, such as those defined in commonly used dictionaries, should be interpreted as having a meaning that is consistent with their meaning in the context of the relevant art and should not be interpreted in an idealized or overly formal sense unless expressly so defined herein.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Hereinafter, some example embodiments will be explained in further detail with reference to the accompanying drawings.

Figure 1B:
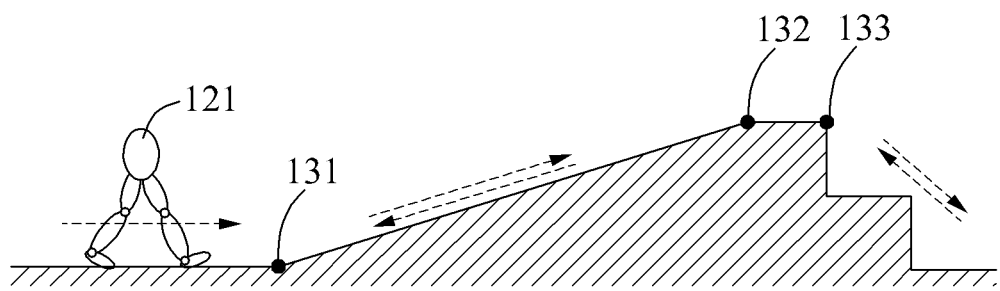

FIGS. 1A and 1B illustrate gait tasks according to an example embodiment.

Referring to FIGS. 1A and 1B, a walking assistance apparatus may be attached to a lower body of a user to assist walking of the user by performing different operations based on gait tasks. For example, as shown in FIG. 1A, when five gait tasks, for example, a level-walking task 111, an inclined-walking task 112, a declined-walking task 113, a stepping-up task 114, and a stepping-down task 115, are defined, the walking assistance apparatus may perform different gait motions based on respective gait tasks. Although FIG. 1 illustrates the five gait tasks, the gait tasks are not limited thereto. In an example, the walking assistance apparatus may include a plurality of operation modes respectively corresponding to a plurality of gait tasks. The walking assistance apparatus may recognize a gait task each time the user walks, and perform an operation mode corresponding to the recognized gait task.

Referring to FIG. 1B, a walking assistance apparatus 121 may operate in a first operation mode based on the level-walking task 111. The walking assistance apparatus 121 may recognize the inclined-walking task 112 at a point 131 by sensing a motion of a user using a sensor attached to the walking assistance apparatus 121 and thus, may change an operation mode to a second operation mode based on the inclined-walking task 112. The walking assistance apparatus 121 may recognize the level-walking task 113 at a point 132 and change the operation mode to the first operation mode. The walking assistance apparatus 121 may recognize the stepping-down task 115 at a point 133 and change the operation mode to a third operation mode based on the stepping-down task 115.

Figure 2:
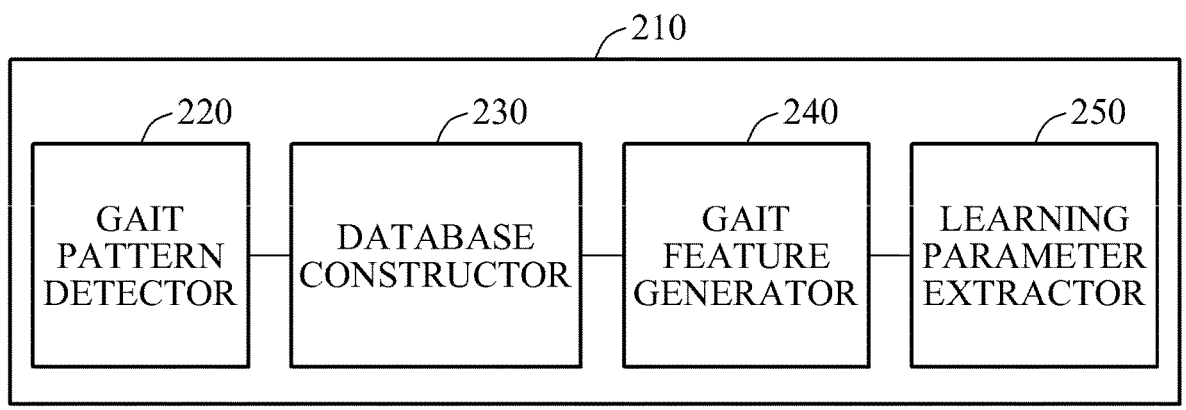
FIG. 2 is a block diagram illustrating a preprocessing apparatus for gait task recognition according to an example embodiment.

FIG. 2 is a block diagram illustrating a preprocessing apparatus for gait task recognition according to an example embodiment.

Figure 3:
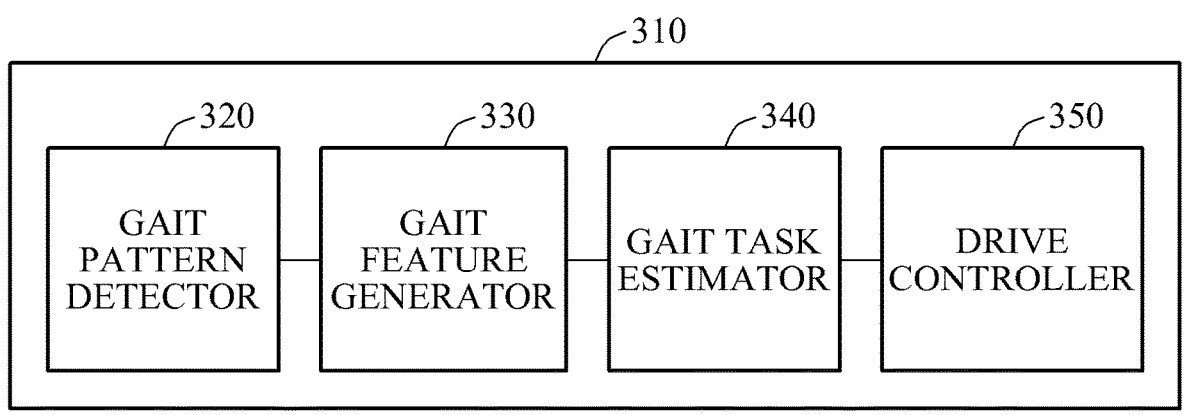
FIG. 3 is a block diagram illustrating a gait task recognition apparatus for recognizing a gait task according to an example embodiment.

Referring to FIG. 2, a preprocessing apparatus 210 may construct a database to be used to recognize a gait task by a gait pattern recognition apparatus 310 which will be described with reference to FIG. 3, and extract a learning parameter with respect to a desired (or alternatively, predetermined) learning model. Although FIGS. 2 and 3 illustrate the preprocessing apparatus 210 and the gait pattern recognition apparatus 310 as different apparatuses, the preprocessing apparatus 210 and the gait pattern recognition apparatus 310 may be included in the same apparatus or may be implemented as different apparatuses.

Referring to FIG. 2, the preprocessing apparatus 210 includes a gait pattern detector 220, a database constructor 230, a gait feature generator 240, and a learning parameter extractor 250.

The gait pattern detector 220 may detect a plurality of gait patterns based on sensed data. For example, the sensed data may refer to data obtained by sensing a change in a bio signal or a quantity of motion of a user with respect to a gait motion using a sensor attached to a walking assistance apparatus. For example, the sensed data may refer to virtual data based on motion data obtained through a simulation. Further, the sensed data may refer to data sensed with respect to a single user, or data sensed with respect to a plurality of users. Depending on a gait task, the sensed data may have an intrinsic pattern. In an example, the sensed data may include at least one of acceleration data sensed by an inertial measurement unit (IMU) sensor, angular velocity data sensed by the IMU sensor, joint angle data sensed by a potentiometer, joint angular velocity data sensed by the potentiometer, and electromyography (EMG) data extracted from an EMG sensor. The acceleration data or the angular velocity data may refer to acceleration data or angular velocity data with respect to at least one of an X axis, a Y axis, and a Z axis. The joint angle data or the joint angular velocity data may refer to joint angle data or joint angular velocity data with respect to at least one of a right (R) axis and a left (L) axis. The sensed data may be extracted from a plurality of IMU sensors, a plurality of potentiometers, or a plurality of EMG sensors. Further, the sensor is not limited to the IMU sensor, the potentiometer, or the EMG sensor, and may include all other sensors that may sense a change in a biosignal or a quantity of motion of a user with respect to a gait motion.

The gait pattern may refer to a pattern to be used to recognize a gait task. A basic unit of the gait pattern may be a step or a stride. The step may include a single heel strike, and the heel strike may indicate a state in which a sole of a user touches the ground. The stride may include two steps. The gait pattern detector 220 may extract a plurality of gait patterns by dividing the sensed data into steps or strides.

The gait pattern detector 220 may extract a step duration based on an angle difference between the R-axis joint angle data and the L-axis joint angle data, and detect a heel strike based on acceleration data with respect to the extracted step duration. For example, the gait pattern detector 220 may extract the step duration as an interval between points at which the angle difference between the R-axis joint angle data and the L-axis joint angle data sharply increases, and extract a plurality of steps by dividing the sensed data by a time duration corresponding to the extracted step duration. The gait pattern detector 220 may verify, for each step, whether acceleration data divided by a time duration corresponding to a step duration of each step include a peak. When the divided acceleration data includes a peak, the gait pattern detector 220 may determine that the corresponding step includes a heel strike, and verify the corresponding step as a valid step. When the acceleration data does not include a peak, the gait pattern detector 220 may determine that the corresponding step does not include a heel strike, and verify the corresponding step as an invalid step.

For example, the gait pattern detector 220 may normalize a plurality of gait patterns with respect to at least one of a time axis and a data axis. The normalization with respect to the time axis may be referred to as a time normalization, and the normalization with respect to the data axis may be referred to as a Z normalization. Because each of the plurality of gait patterns may include a step or a stride, sizes of the plurality of gait patterns with respect to the time axis may differ from each other. Further, because a quantity of motion with respect to a gait may not be uniform each time, sizes of the plurality of gait patterns with respect to the data axis may also differ from each other. The database constructor 230 may store the gait patterns in a database. When the gait patterns have different periods or different data ranges, a database search speed may decrease. Accordingly, the gait pattern detector 220 may perform the time normalization or the Z normalization on the plurality of gait patterns to increase database search efficiency.

According to one example embodiment, the gait pattern detector 220 may perform the time normalization by correcting a time error in the plurality of gait patterns based on a desired (or alternatively, predetermined) period. For example, the gait pattern detector 220 may correct a sampling rate of the plurality of gait patterns at equal intervals based on a desired (or alternatively, predetermined) sampling rate. The gait pattern detector 220 may interpolate the plurality of gait patterns based on the desired (or alternatively, predetermined) period, in view of a linearity of the plurality of gait patterns.

According to another example embodiment, the gait pattern detector 220 may perform the Z normalization based on an average and a standard deviation of the sensed data with respect to each of the plurality of gait patterns. For example, the gait pattern detector 220 may calculate the average and the standard deviation of the sensed data with respect to each of the plurality of gait patterns, and normalize the calculated average and the standard deviation using Equation 1.

$$Z = \frac{x - \mu(x)}{\sigma(x)} \quad \text{[Equation 1]}$$

In Equation 1, z denotes a Z-normalized gait pattern, x denotes the corresponding gait pattern, μ(x) denotes an average of sensed data with respect to the corresponding gait pattern, and σ(x) denotes a standard deviation of the sensed data with respect to the corresponding gait pattern. Accordingly, a difference between data ranges of the plurality of gait patterns may decrease. Such decrease may indicate that an error in data among the plurality of gait patterns occurring due to an individual difference or an environmental difference may decrease. Thus, a gait task recognition performance of the gait pattern recognition apparatus 310 for recognizing a gait task may increase.

The database constructor 230 may construct a plurality of databases by classifying the plurality of gait patterns based on a plurality of gait tasks, and storing the classified plurality of gait patterns as gait data in a plurality of databases respectively corresponding to the plurality of gait tasks. The plurality of databases may refer to separate databases, or a plurality of sub-databases belonging to a single database. According to an example embodiment, the plurality of gait tasks may include a level-walking task, an inclined-walking task, a declined-walking task, a stepping-up task, and a stepping-down task, respectively. However, the plurality of gait tasks is not limited thereto. For example, the plurality of gait tasks may include three gait tasks (e.g., a level-walking task, an inclined-walking task, and a declined-walking task), or may include seven gait tasks, (e.g., a level-walking task, a 15-degree inclined-walking task, a 30-degree inclined-walking task, a 15-degree declined-walking task, a 30-degree declined-walking task, a stepping-up task, and a stepping-down task).

The database constructor 230 may classify the plurality of gait patterns based on the plurality of gait tasks. For example, the database constructor 230 may classify the plurality of gait patterns, respectively, based on a gait task at a time at which data constituting the plurality of gait patterns are sensed. Further, because the sensed data may have an intrinsic pattern based on a gait task, the database constructor 230 may classify the plurality of gait patterns based on the plurality of gait tasks by analyzing the plurality of gait patterns based on intrinsic patterns with respect to gait tasks.

The database constructor 230 may store the classified plurality of gait patterns as gait data in each of the plurality of databases. Accordingly, each of the plurality of databases may include $n_i$ items of gait data. Here, i denotes an index of a gait task.

The database constructor 230 may store the classified plurality of gait patterns as gait data in each of the plurality of databases using a k-d tree structure (short for k-dimensional tree in computer science that is a space-partitioning data structure for organizing points in a k-dimensional space). In this example, a time of $O(n_i \log n_i)$ may be used to store the $n_i$ items of gait data as the gait data in each of the plurality of databases using the k-d tree structure. When the plurality of databases uses the k-d tree structure, a time of may be used to search the plurality of databases for the gait data. Accordingly, the gait task recognition apparatus 310 for recognizing a gait task may search the plurality of databases for the gait data in real time. The database constructor 230 may store the classified plurality of gait patterns as gait data in each of the plurality of databases using a database construction structure other than the k-d tree structure.

The gait feature generator 240 may generate a gait feature with respect to each of the gait data based on similarities among the gait data. For example, the gait feature generator 240 may extract, with respect to each of the gait data, gait data similar to each the gait data. In this example, the gait feature generator 240 may calculate, with respect to each of the gait data, similarities between one gait data and the remaining gait data, which exclude the one gait data, and extract one or more gait data similar to the one gait data with respect to each of the plurality of databases based on calculated similarities. According to an example embodiment, a similarity may be calculated not only based on a distance between one of gait data and another of gait data, but also based on all indices that may indicate a degree of match between the one gait data and each of the remaining gait data. For example, the similarity may be calculated based on a mean value or an intermediate value between a size of the one gait data and a size of each of the remaining gait data, a gait velocity between the one gait data and each of the remaining gait data, a stride length, a root-mean square (RMS) error, a cadence, a walk ratio, or frequency domain information between the one gait data and each of the remaining gait data. The cadence may refer to a value obtained by dividing a number of steps by a desired (or alternatively, predetermined) time. The walk ratio may refer to a value obtained by dividing a step length by a cadence. According to some example embodiments, when the similarity corresponds to the distance between the one gait data and each of the remaining gait data, the gait feature generator 240 may calculate similarities between the one gait data and one or more similar gait data using at least one of an L1 norm, an L2 norm, a normalized cross correlation (NCC), and dynamic time warping (DTW). For example, the gait feature generator 240 may calculate, with respect to each of the plurality of gait data, DTW distances between the one gait data and each of the remaining gait data, which exclude the one gait data, and extract one or more gait data having relatively small DTW distances as gait data having relatively high similarities to the one gait data. The gait feature generator 240 may extract the gait data similar to the one gait data from each of the plurality of databases. Further, the gait feature generator 240 may calculate a mean value of similarities between the one gait data and the one or more gait data similar to the one gait data, and generate a gait feature vector including a feature value corresponding to each of the plurality of gait tasks based on the calculated mean value as an element. For example, when three gait tasks are defined and three databases are provided, the gait feature generator 240 may extract, with respect to each of the three databases, three gait data having relatively high similarities to a first gait data. The gait feature generator 240 may calculate a first mean value corresponding to a mean value of similarities between the first gait data and three similar gait data extracted from a first database, a second mean value corresponding to a mean value of similarities between the first gait data and three similar gait data extracted from a second database, and a third mean value corresponding to a mean value of similarities between the first gait data and three similar gait data extracted from a third database. Accordingly, the first mean value, the second mean value, and the third mean value may indicate feature values of the first gait data corresponding to a first gait task, a second gait task, and a third gait task, respectively. The gait feature generator 240 may generate a 3×1 gait feature vector including the first mean value, the second mean value, and the third mean value as elements. The gait feature generator 240 may generate such a gait feature vector with respect to each gait data included in the plurality of databases.

Further, the gait feature generator 240 may generate a gait feature by normalizing the gait feature vector generated with respect to each gait data. For example, the gait feature generator 240 may generate the gait feature by normalizing gait feature vectors, which are generated with respect to respective gait data included in the plurality of databases, into vectors having the same sizes.

According to an example embodiment, when sensed data with respect to a new user is obtained, the preprocessing apparatus 210 may detect a plurality of gait patterns with respect to the new user based on the sensed data, classify the plurality of gait patterns based on a plurality of gait tasks, and store the classified plurality of gait patterns as gait data in each of the plurality of databases. When a gait data stored in the plurality of databases are not used to recognize a gait task for a certain period of time, the preprocessing apparatus 210 may delete the unused gait data.

The learning parameter extractor 250 may extract a learning parameter with respect to a desired (or alternatively, predetermined) learning model by applying the gait feature with respect to each of the plurality of gait data to the desired (or alternatively, predetermined) learning model. The desired (or alternatively, predetermined) learning model may include one of a neural network (NN) model, a support vector regression (SVR) model, and a Gaussian process regression model. Further, the desired (or alternatively, predetermined) learning model may include other learning models that may estimate a gait task using a feature vector, rather than the NN model, the SVR model, and the Gaussian process regression model. The other learning model may include, for example, a pattern classification based learning model. When the desired (or alternatively, predetermined) learning model is the NN model, the desired (or alternatively, predetermined) learning parameter may include a connection pattern among neurons, a weight, and activation functions. When the desired (or alternatively, predetermined) learning model is the SVR model, the desired (or alternatively, predetermined) learning parameter may include kernel functions, and penalty parameters. When the desired (or alternatively, predetermined) learning model is the Gaussian process regression model, the desired (or alternatively, predetermined) learning parameter may include kernel functions and hyper-parameters.

The learning parameter extractor 250 may map the gait feature with respect to each of the gait data to a feature space of a desired (or alternatively, predetermined) dimension. When the desired (or alternatively, predetermined) learning model is the SVR model, the learning parameter extractor 250 may map the gait feature with respect to each gait data to a feature space using a homogeneous kernel map. For example, the learning parameter extractor 250 may map a 5×1 gait feature to a feature space of 15×1 dimensions using the homogeneous kernel map. The learning parameter extractor 250 may input the mapped gait feature with respect to each gait data into the desired (or alternatively, predetermined) learning model. The learning parameter extractor 250 may extract the learning parameter by applying the gait feature to a non-linear learning model (e.g., a non-linear SVR model) in a space of relatively low dimensions. Accordingly, a calculation time for extracting the learning parameter may decrease. In addition to the homogeneous kernel map, the learning parameter extractor 250 may map the gait feature with respect to each gait data to a feature space using a principle component analysis (PCA) or a linear discriminant analysis (LDA).

The learning parameter extractor 250 may fit the learning parameter to be suitable for gait task recognition by applying the gait feature with respect to each gait data to a desired (or alternatively, predetermined) learning model.

For example, when a desired (or alternatively, predetermined) learning model is the SVR model, the learning parameter extractor 250 may extract learning parameters in relation to gait features with respect to all items of the gait data included in the plurality of databases through learning by designating a class of +1 with respect to a gait task corresponding to the gait features, and designating a class of −1 with respect to a gait task not corresponding to the gait features. In this example, when five gait tasks are defined, the learning parameter extractor 250 may extract learning parameters such as, for example, $$w_{SVM} = \begin{bmatrix} w_{task1} \\ w_{task2} \\ w_{task3} \\ w_{task4} \\ w_{task5} \end{bmatrix}$$

and $$b_{SVM} = \begin{bmatrix} b_{task1} \\ b_{task2} \\ b_{task3} \\ b_{task4} \\ b_{task5} \end{bmatrix}.$$

The learning parameter extractor 250 may transmit the extracted learning parameter to the gait task recognition apparatus 310 using a communication interface. Accordingly, the gait task recognition apparatus 310 may recognize a gait task more accurately and rapidly.

FIG. 3 is a block diagram illustrating a gait task recognition apparatus for recognizing a gait task according to an example embodiment.

Referring to FIG. 3, the gait task recognition apparatus 310 for recognizing a gait task includes a gait pattern detector 320, a gait feature generator 330, a gait task estimator 340, and a drive controller 350.

The gait pattern detector 320 may detect a gait pattern of a user based on sensed data. The sensed data may refer to data obtained by sensing a change in a biosignal or a quantity of motion of the user with respect to a gait motion using a sensor attached to a walking assistance apparatus. Further, the sensed data may refer to virtual data based on motion data obtained through a simulation. Depending on a gait task, the sensed data may have an intrinsic pattern. Thus, the gait task recognition apparatus 310 for recognizing a gait task may estimate a gait task based on the sensed data. In an example, the sensed data may include at least one of acceleration data sensed by an IMU sensor, angular velocity data sensed by the IMU sensor, joint angle data sensed by a potentiometer, joint angular velocity data sensed by the potentiometer, and EMG data extracted from an EMG sensor. In this example, the acceleration data or the angular velocity data may refer to acceleration data or angular velocity data with respect to at least a portion of an X axis, a Y axis, and a Z axis. The joint angle data or the joint angular velocity data may refer to joint angle data or joint angular velocity data with respect to at least a portion of an R axis and an L axis. The sensed data may be extracted from a plurality of IMU sensors, a plurality of potentiometers, or a plurality of EMG sensors.

A basic unit of the gait pattern may be a step or a stride. The step may include a single heel strike, and the stride may include two steps. The gait pattern detector 320 may extract the gait pattern of the user by dividing the sensed data into steps or strides.

The gait pattern detector 320 may extract a step duration based on an angle difference between the R-axis joint angle data and the L-axis joint angle data, and detect a heel strike based on acceleration data with respect to the extracted step duration.

Because the gait pattern detector 320 may detect the gait pattern based on a step or a stride as a basic unit, a uniform gait task recognition performance may be expected although gait conditions, for example, a moving speed of the user and a change in a step, are changed. Thus, the gait pattern detector 320 may recognize the gait pattern of the user robustly against a change in the gait conditions, when compared to a case in which the gait pattern is detected based on a fixed time. Further, the heel strike may be included in a gait motion. When a step includes a single heel strike, a reliability of gait pattern recognition may increase.

The gait task recognition apparatus 310 may recognize a gait task when the gait pattern is detected by the gait pattern detector 320. For example, when the user moves in a stop state, the gait task recognition apparatus 310 may recognize a gait task after a stride including two steps is detected. When the user walks continuously, the gait task recognition apparatus 310 may recognize a gait task each time a single step is detected.

The gait pattern detector 320 may normalize the gait pattern with respect to at least one of a time axis and a data axis. The normalization with respect to the time axis may be referred to as a time normalization, and the normalization with respect to the data axis may be referred to as a Z normalization. Because a gait pattern may include a step or a stride, a size of each gait pattern with respect to the time axis may differ from each other. Further, because a quantity of motion may not be uniform each time a user walks, sizes of gait patterns with respect to the data axis may differ from each other. The gait feature generator 330 may search a database constructed by the preprocessing apparatus 210 of FIG. 2 using the gait pattern. Thus, to increase database search efficiency, the time normalization or the Z normalization may be performed on the gait pattern.

The gait pattern detector 320 may perform the time normalization by correcting a time error in the gait pattern based on a desired (or alternatively, predetermined period. For example, the gait pattern detector 320 may correct a sampling rate of the gait pattern at equal intervals based on a desired (or alternatively, predetermined sampling rate. The gait pattern detector 320 may interpolate the gait pattern based on the desired (or alternatively, predetermined period, in view of a linearity of the gait pattern.

The gait pattern detector 320 may perform the Z normalization based on an average and a standard deviation of the sensed data with respect to the gait pattern. For example, the gait pattern detector 320 may calculate the average and the standard deviation of the sensed data with respect to the gait pattern, and normalize the calculated average and the standard deviation using Equation 1. When the Z normalization is performed, an error in data between gait patterns occurring due to an environmental difference may decrease. Thus, the gait task recognition performance may be improved.

The gait feature generator 330 may extract a plurality of gait data similar to the gait pattern from each of a plurality of databases respectively corresponding to a plurality of gait tasks, and generate a gait feature of the gait pattern based on similarities between the gait pattern and the similar gait data.

The gait feature generator 330 may search each of the plurality of databases to extract the gait data similar to the gait pattern. In this example, the gait feature generator 330 may calculate similarities between the gait pattern and respective gait data included in the plurality of databases, and extract the gait data similar to the gait pattern from each of the plurality of databases based on the calculated similarities. As described above, a similarity may be calculated not only based on a distance between a specific gait data (e.g., the gait pattern detected by the gait pattern detector 320) and each of the remaining gait data excluding the specific gait data, but also based on all indices that may indicate a degree of match between a specific gait data (e.g., the gait pattern detected by the gait pattern detector 320) and each of the remaining gait data excluding the specific gait data.

The gait feature generator 330 may calculate a mean value of the similarities between the gait pattern and the similar gait data, and generate a gait feature vector including a feature value corresponding to each of the plurality of gait tasks based on the calculated mean value as an element. For example, when four gait tasks are defined and four databases are provided, the gait feature generator 330 may extract three similar gait data having relatively high similarities to the gait pattern from gait data included in each of the four databases. The gait feature generator 330 may calculate a first mean value corresponding to a mean value of similarities between the gait pattern and three similar gait data extracted from a first database, a second mean value corresponding to a mean value of similarities between the gait pattern and three similar gait data extracted from a second database, a third mean value corresponding to a mean value of similarities between the gait pattern and three similar gait data extracted from a third database, and a fourth mean value corresponding to a mean value of similarities between the gait pattern and three similar gait data extracted from a fourth database. Accordingly, the first mean value, the second mean value, the third mean value, and the fourth mean value may indicate feature values of the gait pattern corresponding to a first gait task, a second gait task, a third gait task, and a fourth gait task, respectively. The gait feature generator 330 may generate a 4×1 gait feature vector including the first mean value, the second mean value, the third mean value, and the fourth mean value as elements.

The gait feature generator 330 may generate a gait feature by normalizing the gait feature vector.

The gait task estimator 340 may estimate a gait task corresponding to the gait pattern by applying the gait feature to a desired (or alternatively, predetermined learning model. As described above, the desired (or alternatively, predetermined learning model may include one of an NN model, an SVR model, and a Gaussian process regression model. The desired (or alternatively, predetermined learning model may include another learning model that may estimate a gait task using a feature vector, rather than the NN model, the SVR model, and the Gaussian process regression model. The other learning model may include, for example, a pattern classification based learning model.

The gait task estimator 340 may map the gait feature to a feature space of a desired (or alternatively, predetermined) dimension. When the desired (or alternatively, predetermined) learning model is the SVR model, the gait task estimator 340 may map the gait feature to the feature space using a homogeneous kernel map. The gait task estimator 340 may input the mapped gait feature into the desired (or alternatively, predetermined) learning model. The gait task estimator 340 may estimate the gait task by applying the gait feature to a non-linear learning model, for example, a non-linear SVR model, in a space of relatively low dimensions, thereby decreasing a calculation time to be used to estimate the gait task.

The gait task estimator 340 may input the gait feature into the desired (or alternatively, predetermined) learning model, and estimate the gait task corresponding to the gait pattern by applying a desired (or alternatively, predetermined) learning parameter to the desired (or alternatively, predetermined) learning model. The desired (or alternatively, predetermined) learning model may be extracted from the gait data included in each of the plurality of databases. For example, the preprocessing apparatus 210 may fit the learning parameter to be suitable for gait task recognition by applying the gait feature with respect to each of the gait data to the desired (or alternatively, predetermined) learning model. The gait task estimator 340 may input the gait feature into the desired (or alternatively, predetermined) learning model, and estimate the gait task by applying the learning parameter fit by the preprocessing apparatus 210. In this example, the gait task estimator 340 may obtain the learning parameter from the preprocessing apparatus 210 using a communication interface. Accordingly, the gait task estimator 340 may estimate the gait task more rapidly and accurately without performing a separate learning process for learning parameter extraction.

For example, when five gait tasks are defined and the desired (or alternatively, predetermined) learning model is the SVR model, the gait task estimator 340 may apply the gait feature and model parameters $$w_{SVM} = \begin{bmatrix} w_{task1} \\ w_{task2} \\ w_{task3} \\ w_{task4} \\ w_{task5} \end{bmatrix}$$

and $$b_{SVM} = \begin{bmatrix} b_{task1} \\ b_{task2} \\ b_{task3} \\ b_{task4} \\ b_{task5} \end{bmatrix}$$

obtained from the preprocessing apparatus 210 to the SVR model, as expressed by Equation 2.

$$y = w_{SVM} x + b_{SVM} \quad \text{[Equation 2]}$$
$$= [y_{task1} \; y_{task2} \; y_{task3} \; y_{task4} \; y_{task5}]^T$$

In Equation 2, y denotes an output value, $w_{SVM}$ and $b_{SVM}$ denote the model parameters obtained from the preprocessing apparatus 210, x denotes a gait pattern, and $y_{task1}$ through $y_{task5}$ denote a first gait task through a fifth gait task, respectively. The gait task estimator 340 may estimate a gait task corresponding to an item having a maximum value, among items of the output value, as a current gait task.

The drive controller 350 may control a drive of a walking assistance apparatus based on the estimated gait task. For example, when five gait tasks are defined and the gait task estimator 340 estimates the current gait task to be a third gait task, the drive controller 350 may control the drive of the walking assistance apparatus by setting an operation mode of the gait task recognition apparatus 310 to be an operation mode corresponding to the third gait task.

Figure 4:
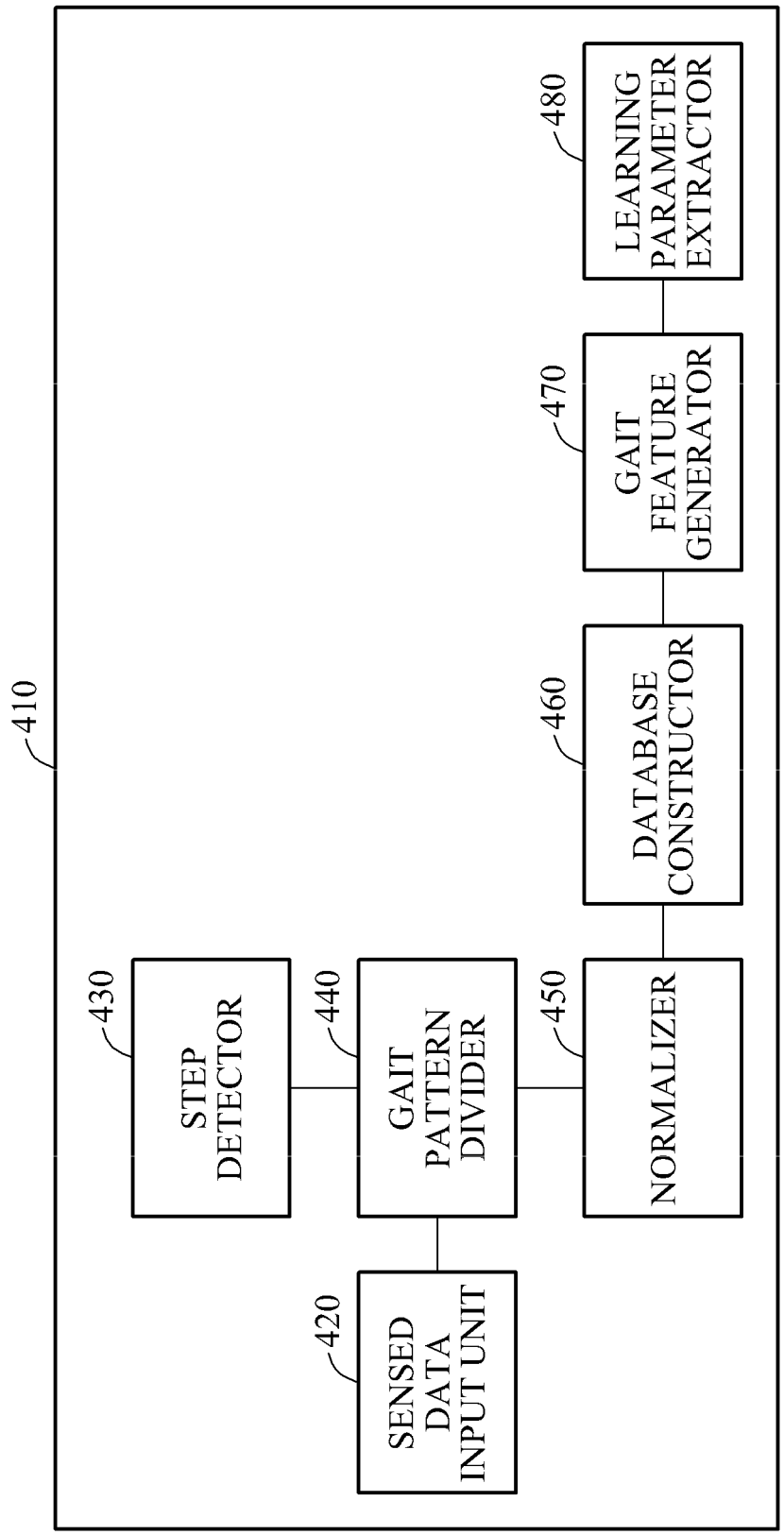
FIG. 4 is a block diagram illustrating a preprocessing apparatus for performing a gait task recognition according to an example embodiment.

FIG. 4 is a block diagram illustrating a preprocessing apparatus for performing a gait task recognition according to an example embodiment.

Referring to FIG. 4, a preprocessing apparatus 410 includes a sensed data input unit 420, a step detector 430, a gait pattern divider 440, a normalizer 450, a database constructor 460, a gait feature generator 470, and a learning parameter extractor 480.

The sensed data input unit 420 may obtain sensed data. The sensed data may be obtained by sensing a change in a biosignal or a quantity of motion of a user with respect to a gait motion using a sensor. The sensed data may include at least one of 3-axis acceleration data sensed by an IMU sensor, 3-axis angular velocity data sensed by the IMU sensor, 2-axis joint angle data sensed by a potentiometer, 2-axis joint angular velocity data sensed by the potentiometer, and EMG data extracted from an EMG sensor. The sensed data may be extracted from a plurality of IMU sensors, a plurality of potentiometers, or a plurality of EMG sensors. In an example, the sensor is not limited to the IMU sensor, the potentiometer, or the EMG sensor, and may include other sensors that may sense a change in a biosignal or a quantity of motion of a user with respect to a gait motion.

The step detector 430 may receive the sensed data from the sensed data input unit 420, and detect a step based on the sensed data. The step detector 430 may extract a step duration by defining an interval between points at which an angle difference between R-axis joint angle data and L-axis joint angle data sharply increases as the step duration. Further, the step detector 430 may verify, for each step, whether acceleration data divided by a time duration corresponding to a step duration include a single peak. When the acceleration data includes a single peak, the step detector 430 may determine that the corresponding step includes a heel strike, and verify the corresponding step as a valid step.

The gait pattern divider 440 may accumulate and store the sensed data received from the sensed data input unit 420. When a step is detected by the step detector 430, the gait pattern divider 440 may divide the accumulated sensed data and extract a plurality of gait patterns.

The normalizer 450 may normalize the plurality of gait patterns with respect to at least one of a time axis and a data axis. When a time normalization is to be performed to normalize the plurality of gait patterns with respect to the time axis, the normalizer 450 may perform the time normalization by correcting a time error in the plurality of gait patterns based on a desired (or alternatively, predetermined) period. When a Z normalization is to be performed to normalize the plurality of gait patterns with respect to the data axis, the normalizer 450 may calculate an average and a standard deviation of the sensed data with respect to each of the plurality of gait patterns, and normalize the calculated average and the standard deviation using Equation 1.

The database constructor 460 may construct a plurality of databases by storing the plurality of gait patterns as gait data in each of the plurality of databases. The plurality of databases may correspond to the plurality of gait tasks, respectively. When i gait tasks are provided, each of the plurality of databases may include $n_i$ items of gait data. In an example, the database constructor 460 may classify the plurality of gait patterns based on the plurality of gait tasks, and store the classified plurality of gait patterns as gait data in each of the plurality of databases using a k-d tree structure. In this example, the database constructor 460 may use a time of $O(n_i \log n_i)$ to store the $n_i$ items of gait data in each of the plurality of databases using the k-d tree structure.

The gait feature generator 470 may generate a gait feature with respect to each gait data based on similarities among the gait data. For example, the gait feature generator 470 may calculate, with respect to each of the gait data, similarities between one gait data and the remaining gait data, which exclude the one gait data, and extract one or more gait data similar to the one gait data with respect to each of the plurality of databases based on the calculated similarities. The gait feature generator 470 may calculate a mean value of similarities between the one gait data and the similar gait data, and generate a gait feature vector including a feature value corresponding to each of the plurality of gait tasks based on the calculated mean value as an element. Further, the gait feature generator 470 may generate the gait feature by normalizing the generated gait feature vector with respect to each gait data.

The learning parameter extractor 480 may extract a learning parameter with respect to a desired (or alternatively, predetermined) learning model by applying the gait feature with respect to each gait data to the desired (or alternatively, predetermined) learning model. For example, the learning parameter extractor 480 may map the gait feature with respect to each gait data to a feature space of a desired (or alternatively, predetermined) dimension, and extract a learning parameter suitable for performing a gait task recognition by applying the mapped gait feature with respect to each gait data to the desired (or alternatively, predetermined) learning model.

Figure 5:
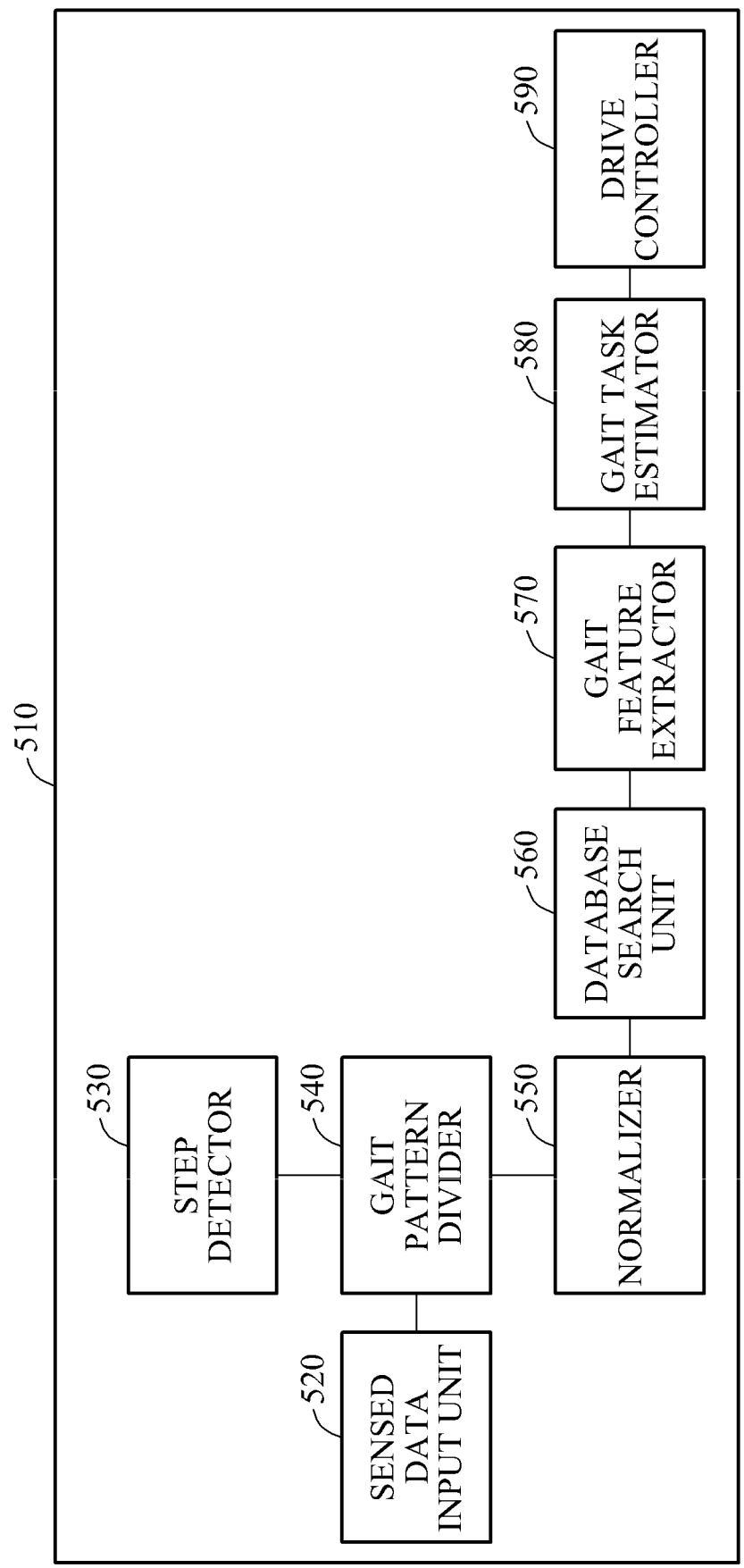
FIG. 5 is a block diagram illustrating a gait task recognition apparatus according to an example embodiment.

FIG. 5 is a block diagram illustrating a gait task recognition apparatus according to an example embodiment.

Referring to FIG. 5, a gait task recognition apparatus 510 includes a sensed data input unit 520, a step detector 530, a gait pattern divider 540, a normalizer 550, a database search unit 560, a gait feature extractor 570, a gait task estimator 580, and a drive controller 590.

The sensed data input unit 520, the step detector 530, the gait pattern divider 540, and the normalizer 550 may perform operations similar to those of the sensed data input unit 420, the step detector 430, the gait pattern divider 440, and the normalizer 450 of FIG. 4, respectively.

The sensed data input unit 520 may obtain sensed data. The sensed data may be obtained by sensing a change in a biosignal or a quantity of motion of a user with respect to a gait motion using a sensor. The sensed data may include at least one of 3-axis acceleration data sensed by an IMU sensor, 3-axis angular velocity data sensed by the IMU sensor, 2-axis joint angle data sensed by a potentiometer, 2-axis joint angular velocity data sensed by the potentiometer, and EMG data extracted from an EMG sensor. The sensed data may be extracted from a plurality of IMU sensors, a plurality of potentiometers, or a plurality of EMG sensors. In an example, the sensor is not limited to the IMU sensor, the potentiometer, or the EMG sensor, and may include all sensors that may sense a change in a biosignal or a quantity of motion of a user with respect to a gait motion.

The step detector 530 may receive the sensed data from the sensed data input unit 520, and detect a step based on the sensed data.

The gait pattern divider 540 may accumulate and store the sensed data received from the sensed data input unit 520. When a step is detected by the step detector 530, the gait pattern divider 540 may divide the accumulated sensed data and extract a gait pattern.

The normalizer 550 may normalize the gait pattern with respect to at least one of a time axis and a data axis. When a time normalization is to be performed to normalize the gait pattern with respect to the time axis, the normalizer 550 may perform the time normalization by correcting a time error in the gait pattern based on a desired (or alternatively, predetermined period). When a Z normalization is to be performed to normalize the gait pattern with respect to the data axis, the normalizer 550 may calculate an average and a standard deviation of the sensed data with respect to the gait pattern, and normalize the calculated average and the standard deviation using Equation 1.

The database search unit 560 may extract gait data similar to the gait pattern from each of the plurality of databases respectively corresponding to the plurality of gait tasks. For example, the database search unit 560 may calculate similarities between the gait pattern and the gait data included in each of the plurality of databases, and extract gait data similar to the gait pattern from each of the plurality of databases based on the calculated similarities. For example, when the plurality of databases is configured based on a k-d tree structure, the database search unit 560 may use a time of $O(\log n_i)$ to extract the gait data similar to the gait pattern from each of the plurality of databases.

The gait feature extractor 570 may calculate a mean value of similarities between the gait pattern and the similar gait data from each of the plurality of databases, and generate a gait feature vector including a feature value corresponding to each of the plurality of gait tasks based on the calculated mean value as an element. Further, the gait feature extractor 570 may generate a gait feature by normalizing the gait feature vector.

The gait task estimator 580 may estimate a gait task corresponding to the gait pattern by applying the gait feature to a desired (or alternatively, predetermined) learning model. For example, the gait task estimator 580 may map the gait feature to a feature space of a desired (or alternatively, predetermined) dimension. When the desired (or alternatively, predetermined) learning model is an SVR model, the gait task estimator 580 may map the gait feature to the feature space using a homogeneous kernel map.

The gait task estimator 580 may input the gait feature into the desired (or alternatively, predetermined) learning model, and estimate the gait task corresponding to the gait pattern by applying a desired (or alternatively, predetermined) learning parameter to the desired (or alternatively, predetermined) learning model. For example, the gait task estimator 580 may receive the desired (or alternatively, predetermined) learning parameter from an external device, for example, the preprocessing apparatus 410 of FIG. 4, using a communication interface. Accordingly, the gait task estimator 580 may estimate the gait task more rapidly and accurately without performing a separate learning process for learning parameter extraction.

The driving controller 590 may control a drive of a walking assistance apparatus based on the estimated gait task. The apparatus 510 for recognizing a gait task may recognize a gait task each time a step is detected by the step detector 530. Thus, the drive controller 590 may control the drive of the walking assistance apparatus by controlling an operation mode in real time.

Figure 6:
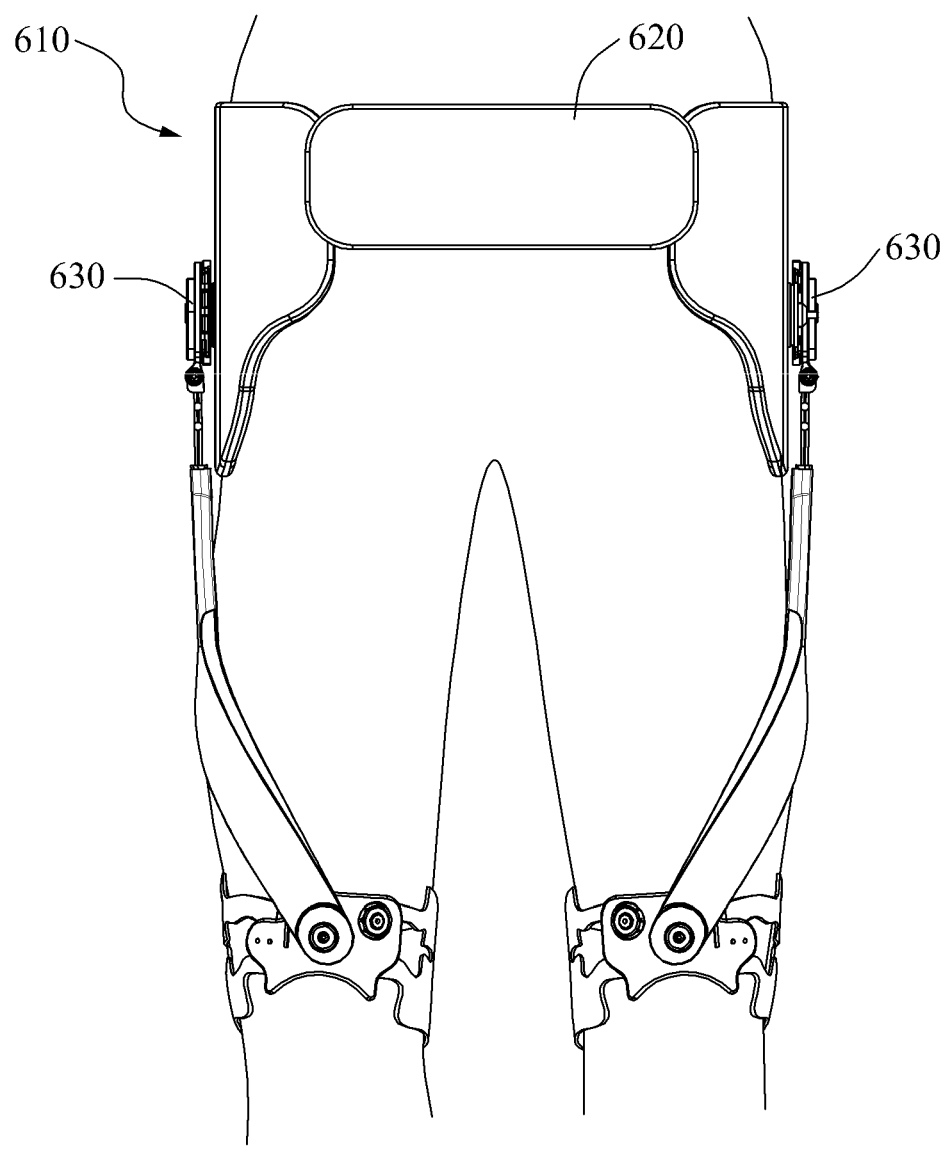
FIG. 6 illustrates sensors according to an example embodiment.

FIG. 6 illustrates sensors according to an example embodiment.

Referring to FIG. 6, a walking assistance apparatus 610 may be attached to a user to assist walking of the user. Although FIG. 6 illustrates an example of a hip-type walking assistance apparatus 610, the walking assistance apparatus 610 may be a different type of walking assistance apparatuses other than the hip-type walking assistance apparatus. For example, descriptions of a walking assistance apparatus provided herein may be applicable to a full-body type walking assistance apparatus.

The walking assistance apparatus 610 includes an IMU sensor 620 and a potentiometer 630. The IMU sensor 620 may sense at least one of variations in an X-axis acceleration, a Y-axis acceleration, and an Z-axis acceleration, and variations in an X-axis angular velocity, a Y-axis angular velocity, and an Z-axis angular velocity. The potentiometer 630 may sense at least one of variations in an R-axis joint angle and an L-axis joint angle, and variations in an R-axis joint angular velocity and an L-axis joint angular velocity. For example, the walking assistance apparatus 610 may include a plurality of IMU sensors 620 and a plurality of potentiometers 630. Further, the walking assistance apparatus 610 may include, in addition to the IMU sensor 620 and the potentiometer 630, another sensor that may sense a change in a biosignal or a quantity of motion of a user with respect to a gait motion. Another sensor may include, for example, an EMG sensor.

Figure 7:
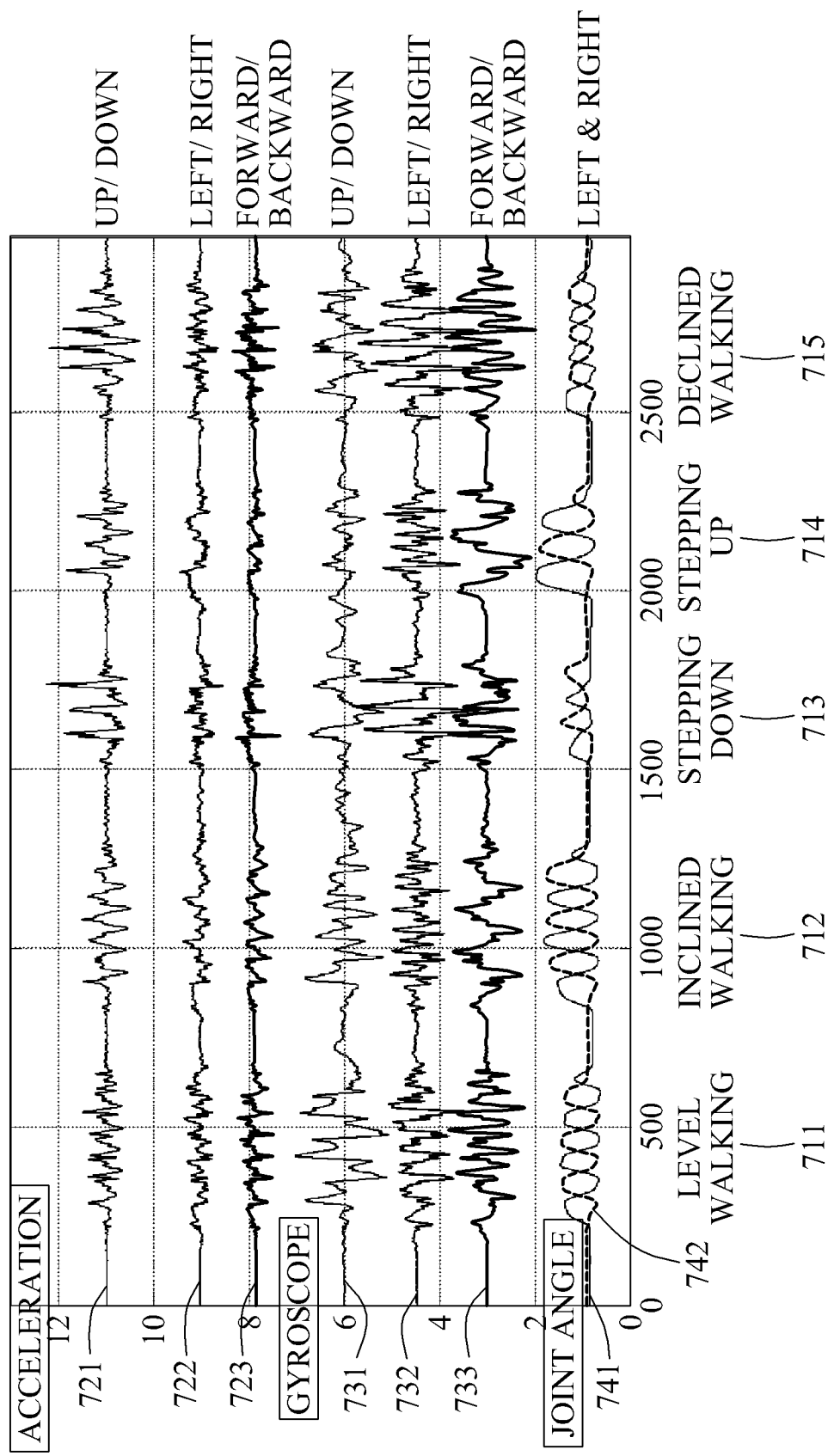
FIG. 7 illustrates sensed data according to an example embodiment.

FIG. 7 illustrates sensed data according to an example embodiment.

Referring to FIG. 7, a graph 710 shows sensed data extracted from sensors attached to a walking assistance apparatus. In the graph 710, a horizontal axis denotes a time, and a vertical axis denotes a size of a corresponding sensed data.

An X-axis acceleration data 721 denotes a variation in acceleration with respect to an up-down motion, a Y-axis acceleration data 722 denotes a variation in acceleration with respect to a left-right motion, and a Z-axis acceleration data 723 denotes a variation in acceleration with respect to a forward-backward motion. An X-axis angular velocity data 731 denotes a variation in angular velocity with respect to an up-down motion, a Y-axis angular velocity data 732 denotes a variation in angular velocity with respect to a left-right motion, and a Z-axis angular velocity data 733 denotes a variation in angular velocity with respect to a frontward-backward motion. Joint angle data 741 and 742 denote variations at joint angles with respect to a left-right motion.

For example, gait tasks may be defined as a level-walking task 711, an inclined-walking task 712, a stepping-down task 713, a stepping-up task 714, and a declined-walking task 715. For example, depending on a gait task, the sensed data may have an intrinsic pattern and thus, a variation in the sensed data may change. For example, the X-axis acceleration data 721 may have a greatest variation in the declined-walking task 715, the X-axis angular velocity data 731 may have a greatest variation in the level-walking task 711, and the joint angle data 741 and 742 may have a greatest variation in the stepping-up task 714.

Figure 8:
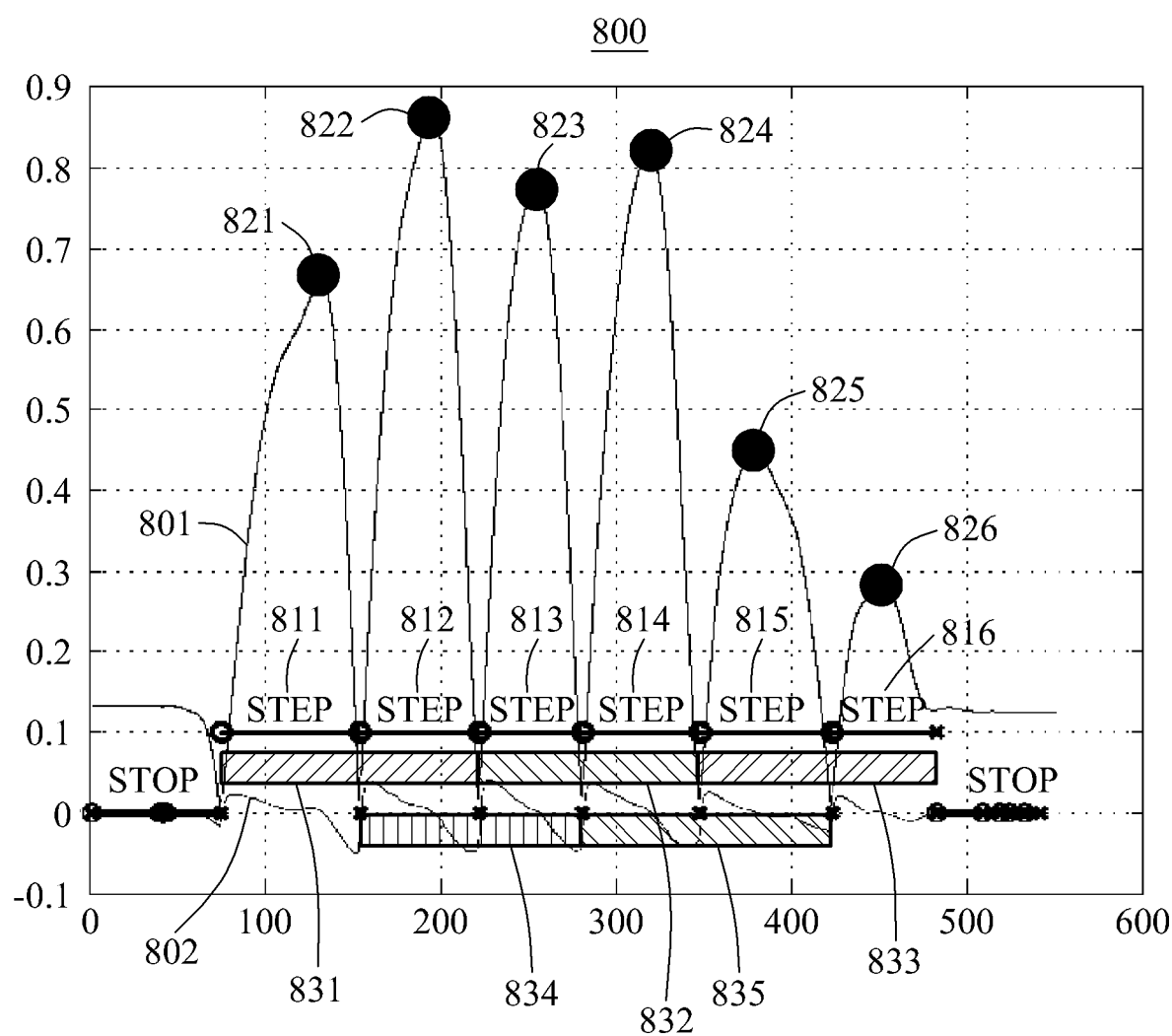
FIG. 8 illustrates a detection of a gait pattern according to an example embodiment.

FIG. 8 illustrates a detection of a gait pattern according to an example embodiment.

Referring to FIG. 8, a horizontal axis of a graph 800 denotes a time, and a vertical axis of the graph 800 denotes a size of a corresponding sensed data.

For example, a gait task recognition apparatus may detect a gait pattern based on acceleration data and joint angle data. The gait task recognition apparatus may extract a step duration based on an angle difference 802 between R-axis joint angle data and L-axis joint angle data. The gait task recognition apparatus may extract steps 811, 812, 813, 814, 815, and 816 by defining an interval between points at which the angle difference 802 sharply increases as the step duration. Further, the gait task recognition apparatus may verify, with respect to each of the steps 811, 812, 813, 814, 815, and 816, whether acceleration data 801 divided by a time duration corresponding to a step duration include a single peak. In the example of FIG. 8, the acceleration data 801 may include a single peak 821, 822, 823, 824, 825, or 826 with respect to a step duration. Accordingly, the gait task recognition apparatus may verify that the extracted steps 811, 812, 813, 814, 815, and 816 are valid. When a basic unit of a gait pattern is a stride, the apparatus for recognizing a gait task may extract strides 831, 832, 833, 834, and 835.

Figure 9A:
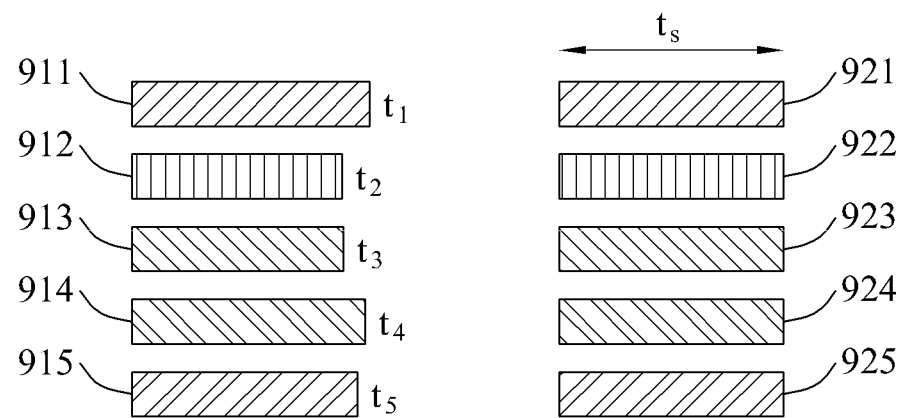
FIGS. 9A and 9B illustrate a normalization of a gait pattern according to an example embodiment.
Figure 9B:
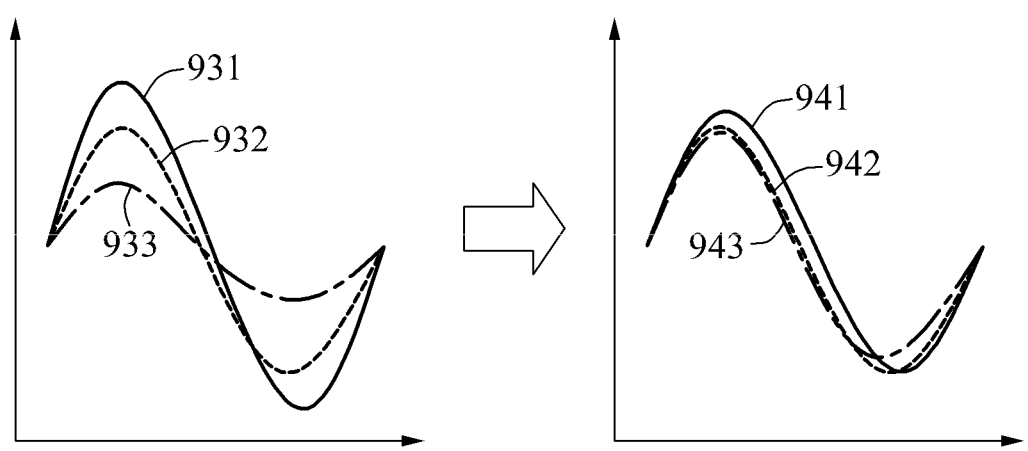

FIGS. 9A and 9B illustrate a normalization of a gait pattern according to an example embodiment.

Referring to FIGS. 9A and 9B, an gait task recognition apparatus may extract gait patterns based on sensed data. Because a gait pattern includes a step or a stride, sizes of the gait patterns with respect to a time axis may differ from each other. Further, because a quantity of motion with respect to a gait is not uniform each time, sizes of the gait patterns with respect to a data axis may also differ from each other. Thus, the gait task recognition apparatus may normalize the gait patterns with respect to at least one of the time axis and the data axis.

In FIG. 9A, timescales of gait patterns 911, 912, 913, 914, and 915 may differ from each other. The gait task recognition apparatus may correct respective timescales $t_1$, $t_2$, $t_3$, $t_4$, and $t_5$ of the gait patterns 911, 912, 913, 914, and 915 to be a desired (or alternatively, predetermined) timescale $t_s$. For example, the gait task recognition apparatus may generate normalized gait patterns 921, 922, 923, 924 and 925 as a result performing a time normalization by interpolating the time axis of the gait patterns 911, 912, 913, 914, and 915.

In FIG. 9B, a horizontal axis of a graph denotes a time and a vertical axis of the graph denotes a size of the sensed data. Gait patterns 931, 932, and 933 may be extracted from data sensed at different points in time in the same gait task. As shown in FIG. 9B, in the same gait task, the gait patterns 931, 932, and 933 may have different data ranges depending on a situation of a user. The gait task recognition apparatus may perform a Z normalization based on an average and a standard deviation of the sensed data with respect to each of the gait patterns 931, 932, and 933. For example, the apparatus for recognizing a gait task may calculate the average and the standard deviation of the sensed data with respect to each of the gait patterns 931, 932, and 933, and normalize the calculated average and the standard deviation using Equation 1. Thus, gait patterns 941, 942, and 943 normalized by the Z normalization may have similar data ranges to each other.

Figure 10:
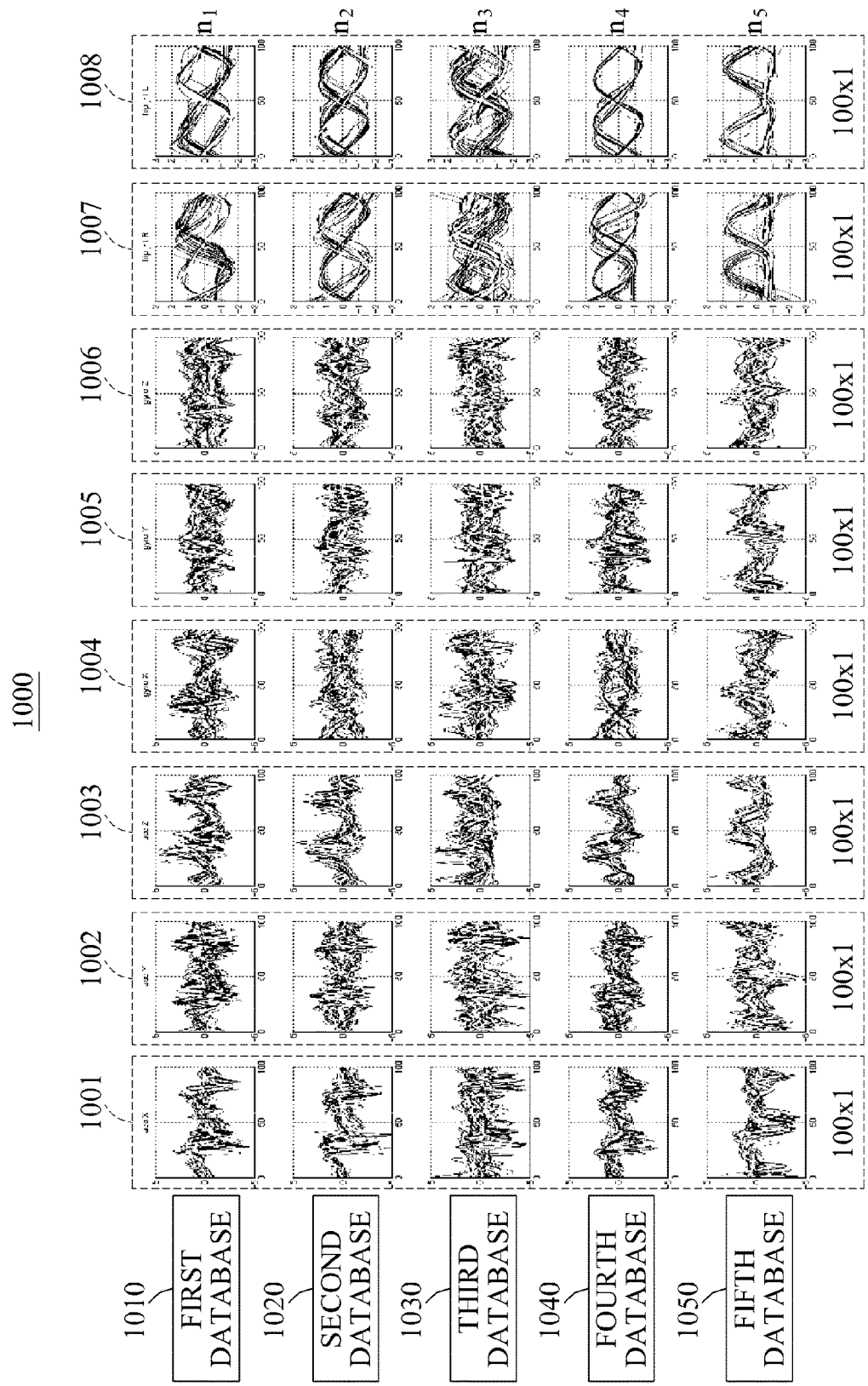
FIG. 10 illustrates databases according to an example embodiment.

FIG. 10 illustrates databases according to an example embodiment.

Referring to FIG. 10, a preprocessing apparatus may construct a plurality of databases 1010, 1020, 1030, 1040, and 1050. The plurality of databases 1010, 1020, 1030, 1040, and 1050 may correspond to a plurality of gait tasks, respectively. Here, the plurality of databases 1010, 1020, 1030, 1040, and 1050 may refer to separate databases, or a plurality of sub-databases belonging to a single database 1000.

The preprocessing apparatus may classify a plurality of gait patterns based on the plurality of gait tasks, and store the classified plurality of gait patterns as gait data in the plurality of databases 1010, 1020, 1030, 1040, and 1050, respectively. For example, gait data 1001, 1002, 1003, 1004, 1005, 1006, 1007, and 1008 may be X-axis acceleration data, Y-axis acceleration data, Z-axis acceleration data, X-axis angular velocity data, Y-axis angular velocity data, Z-axis angular velocity data, R-axis joint angle data, and L-axis joint angle data corresponding to one of the classified plurality of gait patterns. For example, the preprocessing apparatus may store the gait data 1001, 1002, 1003, 1004, 1005, 1006, 1007, and 1008 in form of vectors.

Further, the preprocessing apparatus may construct the plurality of databases 1010, 1020, 1030, 1040, and 1050 using a k-d tree structure. When the databases 1010, 1020, 1030, 1040, and 1050 are constructed based on the k-d tree structure, a time of $O(\log n_i)$ may be used to search the plurality of databases 1010, 1020, 1030, 1040, and 1050 for the gait data. Accordingly, a gait task recognition apparatus may search a plurality of databases for gait data in real time.

Figure 11:
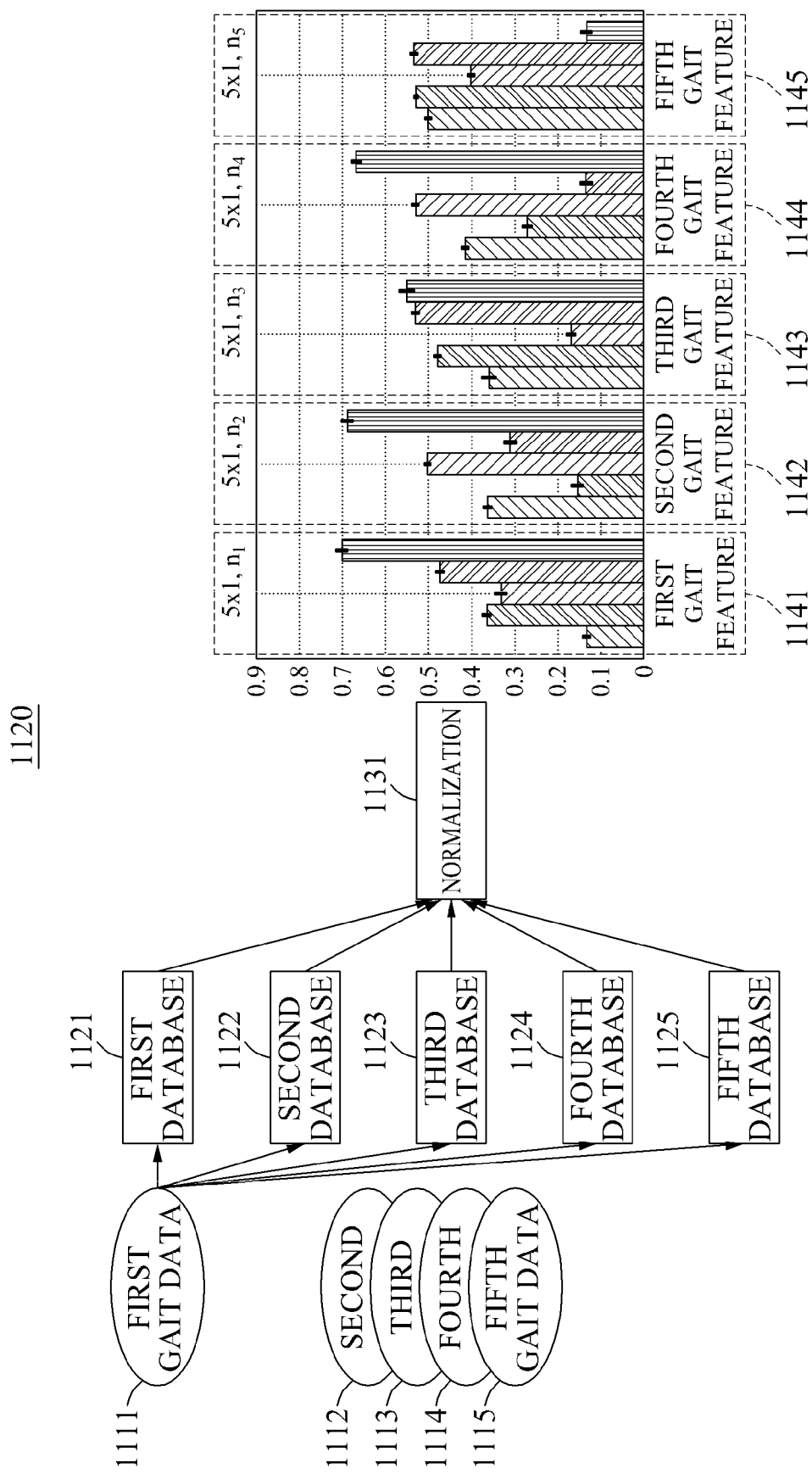
FIG. 11 illustrates an extraction of a gait feature in a preprocessing apparatus for gait task recognition according to an example embodiment.

FIG. 11 illustrates an extraction of a gait feature in a preprocessing apparatus for gait task recognition according to an example embodiment.

Referring to FIG. 11, the preprocessing apparatus may generate a gait feature with respect to each item of gait data based on similarities among the gait data. For example, when five gait tasks are defined, the preprocessing apparatus may construct five databases. To generate a gait feature of first gait data 1111 included in a first database 1121, the preprocessing apparatus may calculate similarities between the first gait data 1111 and the remaining gait data excluding the first gait data 1111 from the first database 1121, and extract gait data similar to the first gait data 1111 from the first database 1121 based on the calculated similarities. The preprocessing apparatus may calculate similarities between the first gait data 1111 and the remaining gait data, which exclude the first gait data 1111, included in each of a second database 1122 through a fifth database 1125, and extract gait data similar to the first gait data 1111 from each of the second database 1122 through the fifth database 1125 based on the calculated similarities.

The preprocessing apparatus may calculate a mean value of the similarities between the first gait data 1111 and the similar gait data extracted from each of the first database 1121 through the fifth database 1125, and generate a first gait feature vector based on the calculated mean value as an element. For example, the preprocessing apparatus may configure a first mean value through a fifth mean value respectively corresponding to the first database 1121 through the fifth database 1125 as a first element through a fifth element of the first gait feature vector. The preprocessing apparatus may generate a first gait feature 1141 by performing a normalization 1131 on the first gait feature vector. Similar to the first gait data 1111, the preprocessing apparatus may generate a second gait feature 1142 through a fifth gait feature 1145 with respect to second gait data 1112 through fifth gait data 1115, respectively.

Figure 12:
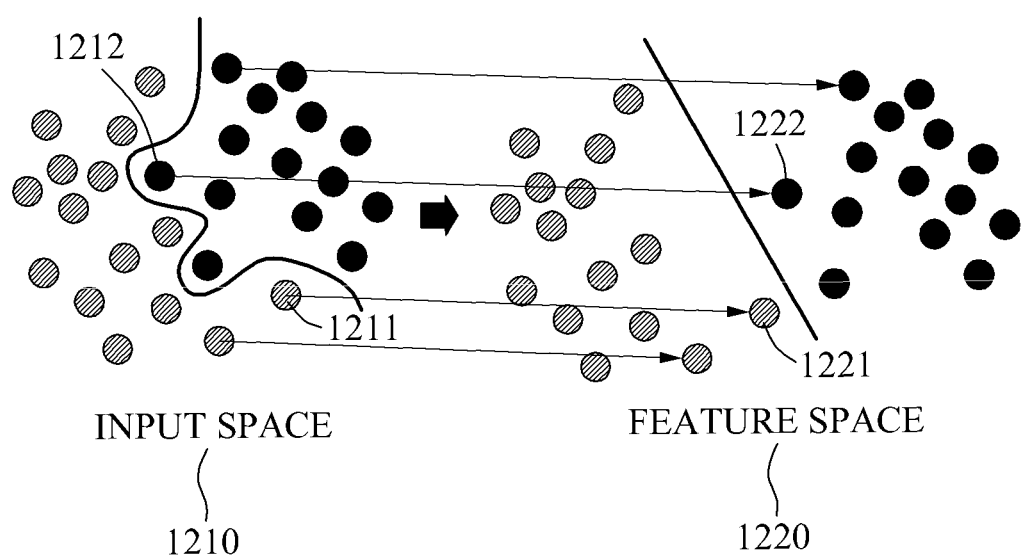
FIG. 12 illustrates mapping of a gait feature to a feature space according to an example embodiment.

FIG. 12 illustrates mapping of a gait feature to a feature space according to an example embodiment.

Referring to FIG. 12, an input space 1210 may include 5×1 gait features. A gait feature 1211 and a gait feature 1212 may correspond to different gait tasks. However, in the input space 1210, the gait feature 1211 and the gait feature 1212 may not be distinguished from each other.

A gait task recognition apparatus may map the gait features 1211 and 1212 to a feature space 1220 of a desired (or alternatively, predetermined) dimension. When the gait task recognition apparatus estimates a gait task using an SVR model, the gait task recognition apparatus may map the gait features 1211 and 1212 to the feature space 1220 of 15×1 dimensions using a homogeneous kernel map. When the gait features 1211 and 1212 are mapped to the feature space 1220, gait features 1221 and 1222 may be distinguished from each other in the feature space 1220. Thus, the gait task recognition apparatus may estimate a gait task by applying a gait feature to a non-linear SVR model in a space of relatively low dimensions, whereby a calculation time to be used to estimate a gait task may decrease.

Figure 13:
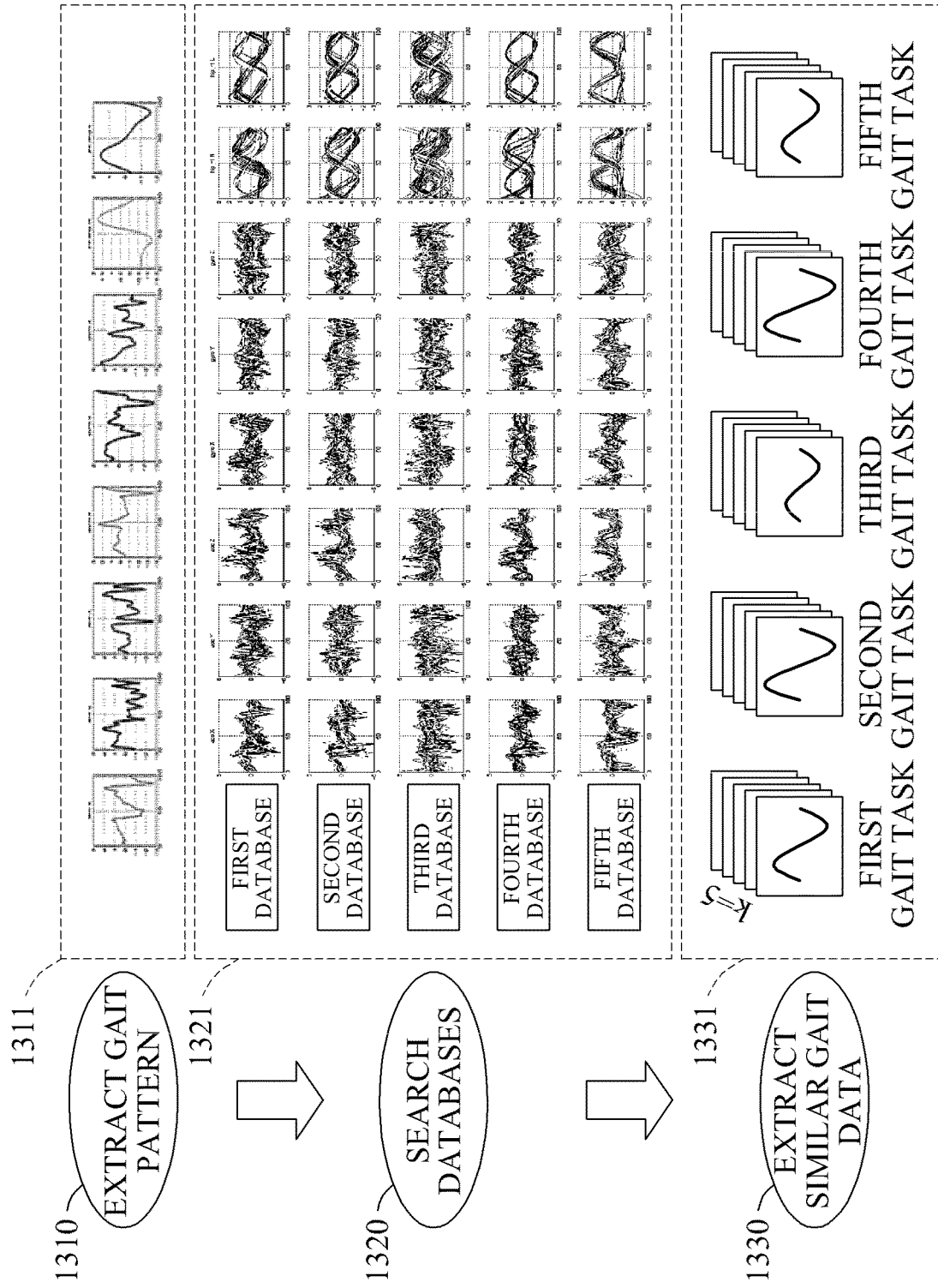
FIG. 13 illustrates a database search according to an example embodiment.

FIG. 13 illustrates a database search according to an example embodiment.

Referring to FIG. 13, a gait task recognition apparatus may extract a gait pattern based on sensed data, in operation 1310. For example, when a user starts to walk in a stop state, the gait task recognition apparatus may extract a gait pattern 1311 based on the sensed data.

The gait task recognition apparatus may search a plurality of databases 1321 based on the gait pattern 1311, in operation 1320, and extract gait data similar to the gait pattern 1311 from each of the plurality of databases 1321 respectively corresponding to a plurality of gait tasks, in operation 1330. For example, the gait task recognition apparatus may search the plurality of databases 1321 using a k-nearest neighbor search. For example, when the plurality of databases 1321 is configured based on a k-d tree structure, a time of $O(\log n_i)$ may be used to search the plurality of databases 1321. Here, $n_i$ denotes a number of items of gait data included in each of the plurality of databases 1321, and i denotes an index of a corresponding one of the plurality of databases 1321. For example, the gait task recognition apparatus may extract five similar gait data 1331 from each of the plurality of databases 1321.

Figure 14:
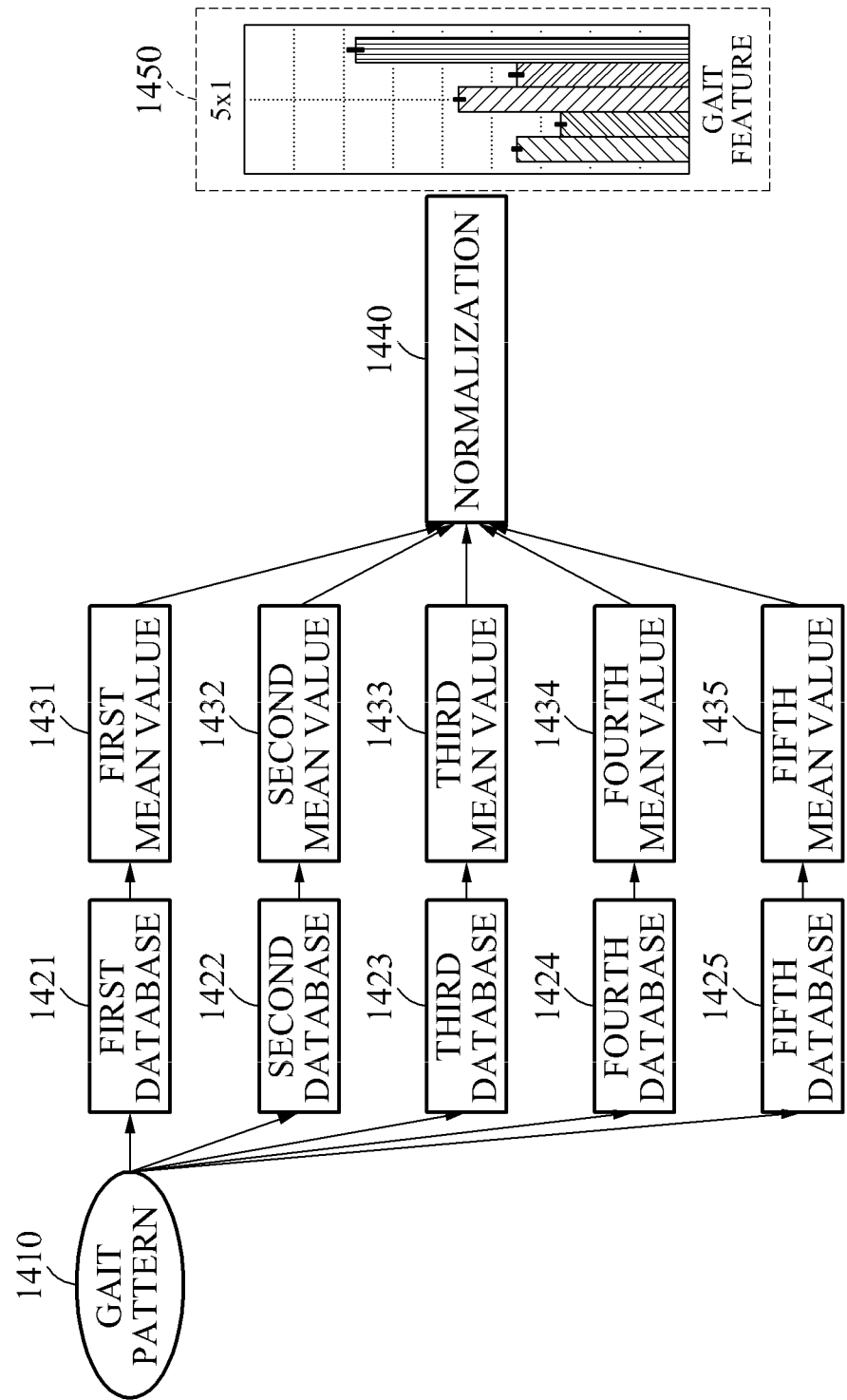
FIG. 14 illustrates an extraction of a gait feature in a gait task recognition apparatus according to an example embodiment.

FIG. 14 illustrates an extraction of a gait feature in a gait task recognition apparatus according to an example embodiment.

Referring to FIG. 14, the gait task recognition apparatus may calculate similarities between a gait pattern 1410 and similar gait data included in each of five databases 1421, 1422, 1423, 1424, and 1425. For example, the gait task recognition apparatus may extract five gait data having relatively high similarities to the gait pattern 1410 from each of the five databases 1421, 1422, 1423, 1424, and 1425, and calculate similarities between the gait pattern 1410 and five similar gait data included in each of the five databases 1421, 1422, 1423, 1424, and 1425.

The gait task recognition apparatus may calculate a mean value of the calculated similarities. For example, the apparatus for recognizing a gait task may calculate a first mean value 1431 corresponding to a mean value of similarities between the gait pattern 1410 and the five similar gait data extracted from the first database 1421. The gait task recognition apparatus may calculate a second mean value 1432 through a fifth mean value 1435 corresponding to mean values of similarities between the gait pattern 1410 and respective five similar gait data extracted from the second database 1422 through the fifth database 1425. The gait task recognition apparatus may configure the first mean value 1431 through the fifth mean value 1435 as a first element through a fifth element of a gait feature vector, respectively.

The apparatus for recognizing a gait task may generate a gait feature 1450 by performing a normalization 1440 on the gait feature vector.

Figure 15:
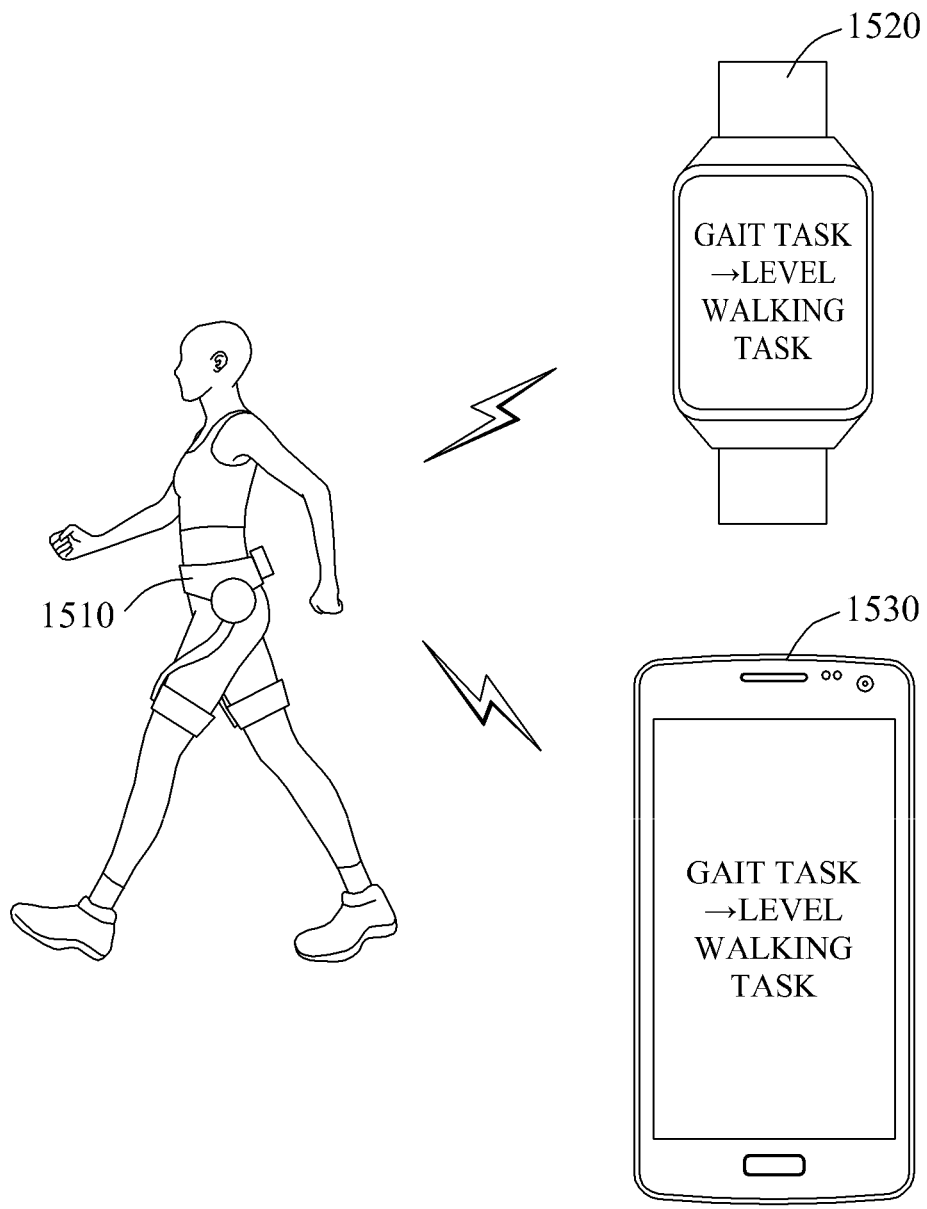
FIG. 15 illustrates an example of a gait task recognition apparatus according to an example embodiment.

FIG. 15 illustrates an example of a gait task recognition apparatus according to an example embodiment.

Referring to FIG. 15, a gait task recognition apparatus 1510 may be included in a walking assistance apparatus. When a user walks, the gait task recognition apparatus 1510 may obtain sensed data. The sensed data may refer to data obtained by sensing a change in a biosignal or a quantity of motion of the user with respect to a gait motion from a sensor included in the gait task recognition apparatus 1510. The gait task recognition apparatus 1510 may detect a gait pattern of the user based on the sensed data, and extract gait data similar to the detected gait pattern from each of a plurality of databases corresponding to each of a plurality of gait tasks. The gait task recognition apparatus 1510 may calculate similarities between the gait pattern and the extracted similar gait data, and generate a gait feature of the gait pattern based on the calculated similarities. The gait task recognition apparatus 1510 may estimate a gait task corresponding to the gait pattern by applying the gait feature to a desired (or alternatively, predetermined) learning model. The gait task recognition apparatus 1510 may control a drive of the walking assistance apparatus based on the estimated gait task. Further, the gait task recognition apparatus 1510 may communicate with a wearable device 1520 or a mobile terminal 1530 using a communication interface. For example, when the gait task recognition apparatus 1510 estimates a gait task, the gait task recognition apparatus 1510 may transmit information about the estimated gait task to the wearable device 1520 or the mobile terminal 1530.

Figure 16:
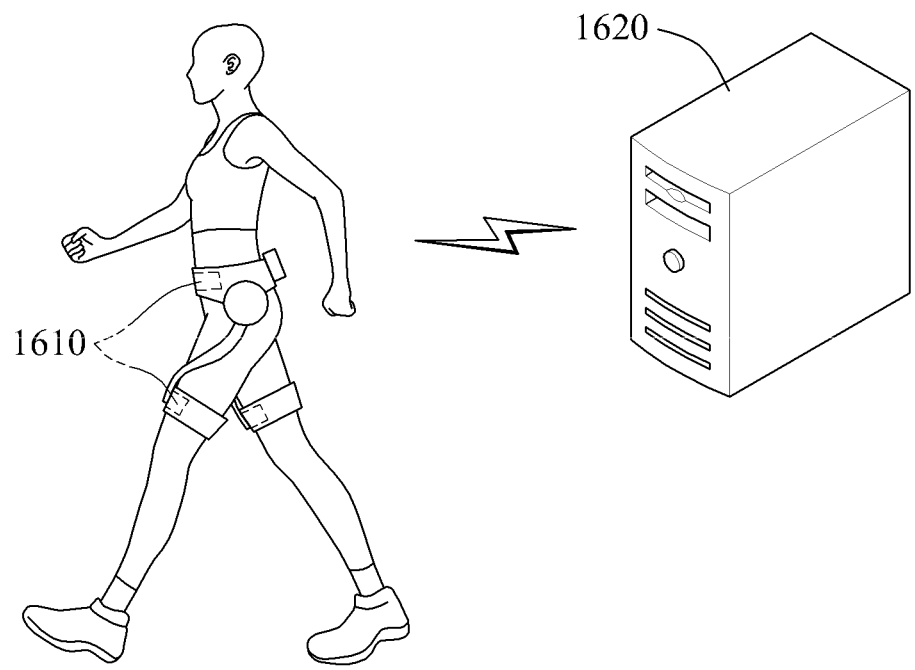
FIG. 16 illustrates an example of a gait task recognition apparatus according to an example embodiment.

FIG. 16 illustrates an example of a gait task recognition apparatus according to an example embodiments.

Referring to FIG. 16, a gait task recognition apparatus 1610 may be included in a walking assistance apparatus. When a user walks, the gait task recognition apparatus 1610 may obtain sensed data. The sensed data may refer to data obtained by sensing a change in a biosignal or a quantity of motion of the user with respect to a gait motion from a sensor included in the gait task recognition apparatus 1610. The gait task recognition apparatus 1610 may detect a gait pattern of the user based on the sensed data. A server 1620 may include a plurality of databases respectively corresponding to a plurality of gait tasks. For example, the plurality of databases may be pre-generated by a preprocessing apparatus, and stored in the server 1620. The gait task recognition apparatus 1610 may search the plurality of databases included in the server 1620 based on the detected gait pattern using a communication interface. The gait task recognition apparatus 1610 may extract gait data similar to the gait pattern from each of the plurality of databases, and generate a gait feature of the gait pattern based on similarities between the gait pattern and the similar gait data.

The gait task recognition apparatus 1610 may obtain a desired (or alternatively, predetermined) learning parameter from the server 1620. The gait task recognition apparatus 1610 may input the gait feature into a desired (or alternatively, predetermined) learning model, and estimate a gait task corresponding to the gait pattern by applying the desired (or alternatively, predetermined) learning parameter obtained from the server 1620 to the desired (or alternatively, predetermined) learning model.

For example, the gait task recognition apparatus 1610 may transmit information about the estimated gait task to the server 1620 using the communication interface.

Figure 17:
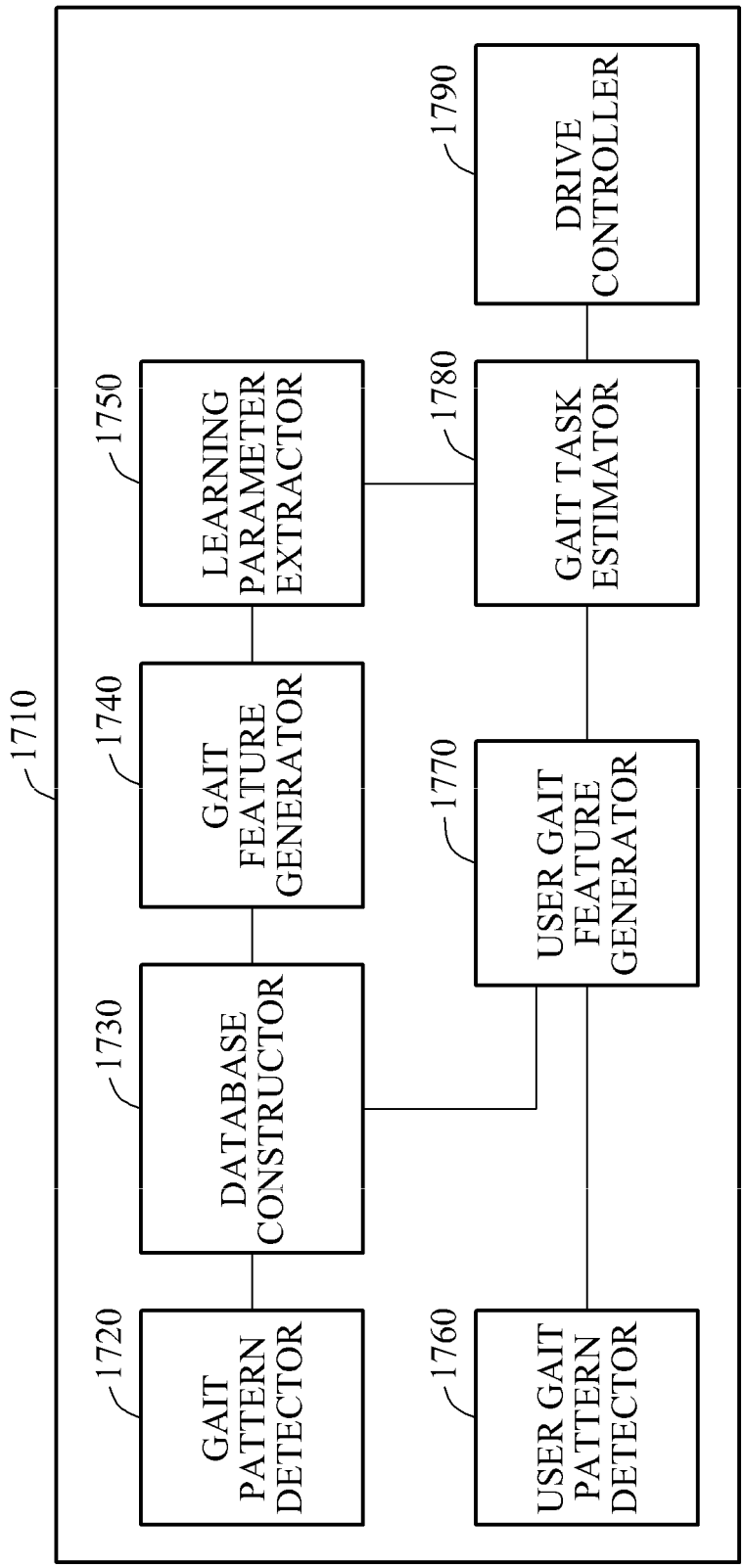
FIG. 17 is a block diagram illustrating a gait task recognition apparatus according to an example embodiment.

FIG. 17 is a block diagram illustrating a gait task recognition apparatus according to an example embodiment.

Referring to FIG. 17, the gait task recognition apparatus 1710 includes a gait pattern detector 1720, a database constructor 1730, a gait feature generator 1740, a learning parameter extractor 1750, a user gait pattern detector 1760, a user gait feature generator 1770, a gait task estimator 1780, and a drive controller 1790.

The gait pattern detector 1720 may detect a plurality of gait patterns based on first sensed data.

The database constructor 1730 may classify the plurality of gait patterns based on a plurality of gait tasks, and store the classified plurality of gait patterns as gait data in each of a plurality of databases corresponding to each of the plurality of gait tasks.

The gait feature generator 1740 may generate a gait feature with respect to each gait data based on similarities among the gait data.

The learning parameter extractor 1750 may extract a learning parameter with respect to a desired (or alternatively, predetermined) learning model by applying the gait feature with respect to each gait data to the desired (or alternatively, predetermined) learning model.

The user gait pattern detector 1760 may detect a gait pattern of a user based on second sensed data.

The user gait feature generator 1770 may extract gait data similar to the gait pattern of the user from each of the plurality of databases, and generate a gait feature of the gait pattern of the user based on similarities between the gait pattern of the user and the similar gait data.

The gait task estimator 1780 may estimate a gait task corresponding to the gait pattern of the user by applying the gait feature of the user to the desired (or alternatively, predetermined) learning model.

The drive controller 1790 may control a drive of a walking assistance apparatus based on the estimated gait task.

The descriptions provided with reference to FIGS. 1A through 16 may be applicable to the gait task recognition apparatus 1710 as shown in FIG. 17 and thus, detailed descriptions will be omitted for conciseness.

Figure 18:
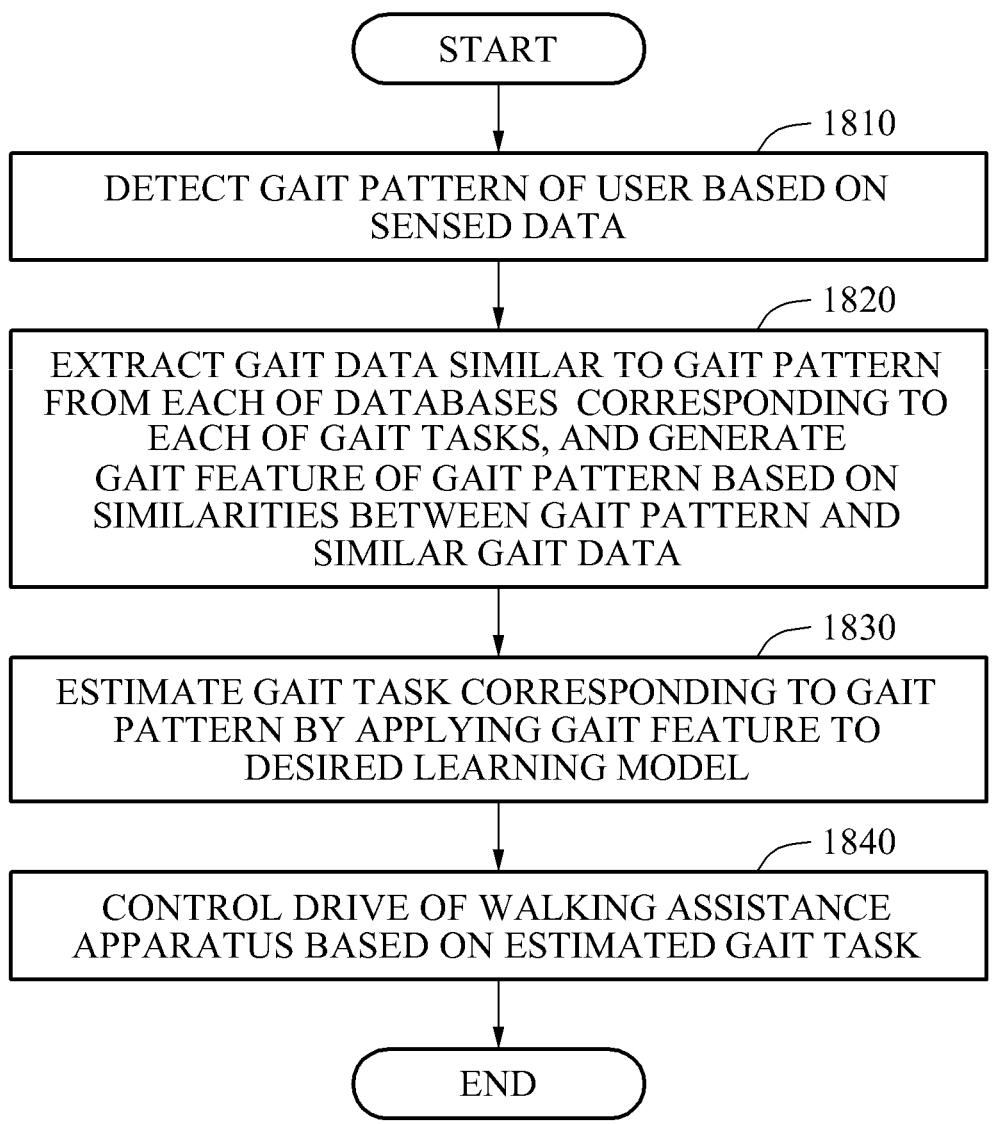
FIG. 18 is a flowchart illustrating a method of recognizing a gait task according to an example embodiment.

FIG. 18 is a flowchart illustrating a method of recognizing a gait task according to an example embodiment.

Referring to FIG. 18, in operation 1810, a gait task recognition apparatus may detect a gait pattern of a user based on sensed data.

In operation 1820, the gait task recognition apparatus may extract gait data similar to the gait pattern from each of a plurality of databases corresponding to each of a plurality of gait tasks, and generate a gait feature of the gait pattern based on similarities between the gait pattern and the similar gait data.

In operation 1830, the gait task recognition apparatus may estimate a gait task corresponding to the gait pattern by applying the gait feature to a desired (or alternatively, predetermined) learning model.

In operation 1840, the gait task recognition apparatus may control a drive of a walking assistance apparatus based on the estimated gait task.

The descriptions provided with reference to FIGS. 1A through 16 may be applicable to the method of recognizing a gait task as shown in FIG. 18 and thus, detailed descriptions will be omitted for conciseness.

Figure 19:
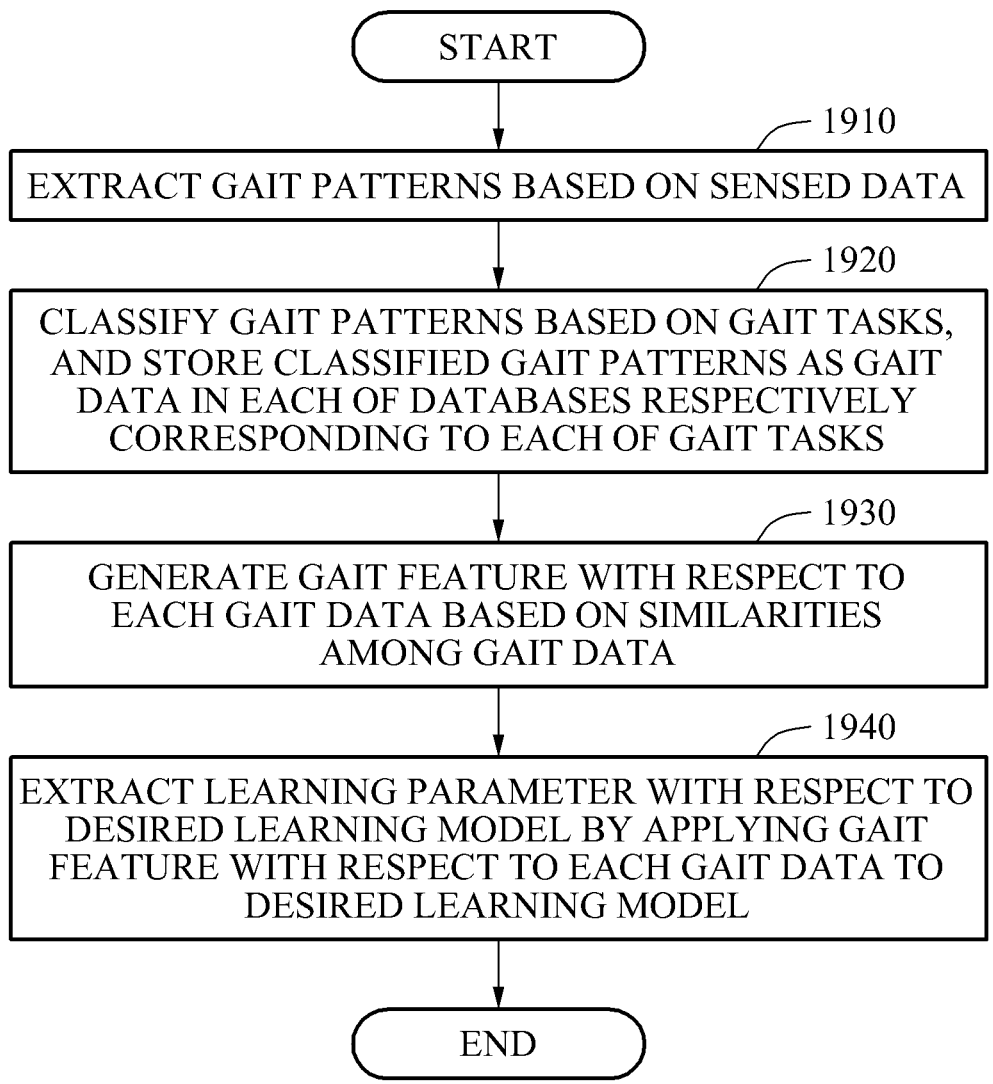
FIG. 19 is a flowchart illustrating a preprocessing method for gait task recognition according to an example embodiment.

FIG. 19 is a flowchart illustrating a preprocessing method for gait task recognition according to an example embodiment.

Referring to FIG. 19, in operation 1910, a preprocessing apparatus may detect a plurality of gait patterns based on sensed data.

In operation 1920, the preprocessing apparatus may classify the plurality of gait patterns based on a plurality of gait tasks, and store the classified plurality of gait patterns as gait data in each of a plurality of databases corresponding to each of the plurality of gait tasks.

In operation 1930, the preprocessing apparatus may generate a gait feature with respect to each gait data based on similarities among the gait data.

In operation 1940, the preprocessing apparatus may extract a learning parameter with respect to a desired (or alternatively, predetermined) learning model by applying the gait feature with respect to each gait data to the desired (or alternatively, predetermined) learning model.

The descriptions provided with reference to FIGS. 1A through 16 may be applicable to the preprocessing method for gait task recognition as shown in FIG. 19 and thus, detailed descriptions will be omitted for conciseness.

FIG. 20 is a flowchart illustrating a method of recognizing a gait task according to an example embodiment.

Referring to FIG. 20, in operation 2010, a gait task recognition apparatus may detect a plurality of gait patterns based on first sensed data.

In operation 2020, the gait task recognition apparatus may classify the plurality of gait patterns based on a plurality of gait tasks, and store the classified plurality of gait patterns as gait data in each of a plurality of databases corresponding to each of the plurality of gait tasks.

In operation 2030, the gait task recognition apparatus may generate a gait feature with respect to each gait data based on similarities among the gait data.

In operation 2040, the gait task recognition apparatus may extract a learning parameter with respect to a desired (or alternatively, predetermined) learning model by applying the gait feature with respect to each gait data to the desired (or alternatively, predetermined) learning model.

In operation 2050, the gait task recognition apparatus may detect a gait pattern of a user based on second sensed data.

In operation 2060, the gait task recognition apparatus may extract gait data similar to the gait pattern of the user from each of the plurality of databases, and generate a gait feature of the gait pattern of the user based on similarities between the gait pattern of the user and the similar gait data.

In operation 2070, the gait task recognition apparatus may estimate a gait task corresponding to the gait pattern of the user by applying the gait feature of the user to the desired (or alternatively, predetermined) learning model.

In operation 2080, the gait task recognition apparatus may control a drive of a walking assistance apparatus based on the estimated gait task.

The descriptions provided with reference to FIGS. 1A through 16 may be applicable to the method of recognizing a gait task as shown in FIG. 20 and thus, detailed descriptions will be omitted for conciseness.

The units and/or modules described herein may be implemented using hardware components and/or software components. For example, the hardware components may include microphones, amplifiers, band-pass filters, audio to digital convertors, and processing devices. A processing device may be implemented using one or more hardware devices configured to carry out and/or execute program code by performing arithmetical, logical, and input/output operations. The processing device(s) may include a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and/or one or more software applications that run on the OS. The processing device also may access, store, manipulate, process, and create data in response to execution of the software. For purpose of simplicity, the description of a processing device is used as singular; however, one skilled in the art will appreciated that a processing device may include multiple processing elements and/or multiple types of processing elements. For example, a processing device may include multiple processors or a processor and a controller. Further, different processing configurations are possible, such a parallel processors.

The software may include a computer program, a piece of code, an instruction, or some combination thereof, to independently or collectively instruct and/or configure the processing device to operate as desired, thereby transforming the processing device into a special purpose processor. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. The software and data may be stored by one or more non-transitory computer readable recording mediums.

The methods according to the above-described example embodiments may be recorded in non-transitory computer-readable media including program instructions to implement various operations of the above-described example embodiments. The media may also include, alone or in combination with the program instructions, data files, data structures, and the like. The program instructions recorded on the media may be those specially designed and constructed for the purposes of example embodiments, or they may be of the kind well-known and available to those having skill in the computer software arts. Examples of non-transitory computer-readable media include magnetic media such as hard disks, floppy disks, and magnetic tape; optical media such as CD-ROM discs, DVDs, and/or Blue-ray discs; magneto-optical media such as optical discs; and hardware devices that are specially configured to store and perform program instructions, such as read-only memory (ROM), random access memory (RAM), flash memory (e.g., USB flash drives, memory cards, memory sticks, etc.), and the like. Examples of program instructions include both machine code, such as produced by a compiler, and files containing higher level code that may be executed by the computer using an interpreter. The above-described devices may be configured to act as one or more software modules in order to perform the operations of the above-described example embodiments, or vice versa.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A walking assistance apparatus comprising:
   at least one sensor configured to generate sensed data by sensing gait motion of a user;
   one or more processors configured to determine a specific gait task, from among a plurality of gait tasks, based on the sensed data; and
   a drive controller configured to drive the walking assistance apparatus based on the determined gait task and the sensed data,
   wherein the one or more processors configured to,
      generate a current gait pattern based on the sensed data,
      generate a gait feature corresponding the current gait pattern based on a plurality of databases corresponding to a plurality of gait tasks, and
      determine the specific gait task corresponding to the current gait pattern, among the plurality of gait tasks, based on the gait feature.

2. The walking assistance apparatus of claim 1, wherein the one or more processors are further configured to search the plurality of databases corresponding the plurality of gait tasks, respectively, for similar gait patterns for the current gait pattern, and
   the gait feature is generated by generating the gait feature corresponding the current gait pattern based on similarities between the current gait pattern and the similar gait patterns.

3. The walking assistance apparatus of claim 2, wherein the gait feature is a vector having dimensions of a number of the plurality of gait tasks, and each of the dimensions of the vector represents a similarity between the current gait pattern and a portion of the similar gait patterns of each of the plurality of gait tasks.

4. The walking assistance apparatus of claim 3, wherein the one or more processors are further configured to normalize the vector of the gait feature.

5. The walking assistance apparatus of claim 3, wherein the one or more processors are further configured to calculate similarities between the current gait pattern and similar gait patterns included in each of the plurality of databases, using at least one of an L1 norm, an L2 norm, a normalized cross correlation (NCC), or dynamic time warping (DTW).

6. The walking assistance apparatus of claim 1, wherein the one or more processors are further configured to,
   input the gait feature into a set learning model, and
   determine the gait task corresponding to the current gait pattern by applying a set learning parameter to the set learning model.

7. The walking assistance apparatus of claim 6, wherein the set learning parameter is extracted from gait patterns as gait data included in each of the plurality of databases based on the set learning model.

8. The walking assistance apparatus of claim 6, wherein the one or more processors are further configured to obtain the set learning parameter from a server.

9. The walking assistance apparatus of claim 1, wherein the one or more processors are further configured to sense a heel strike indicating a state in which a sole of the user touches a ground from the sensed data, and detect the current gait pattern based on a basic unit of one of a step including a single heel strike or a stride including two steps.

10. The walking assistance apparatus of claim 1, wherein the sensed data comprises at least one of acceleration data sensed by an inertial measurement unit (IMU) sensor, angular velocity data sensed by the IMU sensor, joint angle data sensed by a potentiometer, joint angular velocity data sensed by the potentiometer, or electromyography (EMG) data extracted from an EMG sensor.

11. The walking assistance apparatus of claim 1, wherein the one or more processors are further configured to normalize the current gait pattern with respect to at least one of a time axis or a data axis.

12. The walking assistance apparatus of claim 1, wherein the one or more processors are further configured to,
   map the gait feature to a feature space of a set dimension, and
   input the mapped gait feature into a set learning model.

13. A method, performed by an apparatus including one or more processors, for recognizing a gait task and driving a walking assistance apparatus, the method comprising:
   generating, by the one or more processors, a current gait pattern based on sensed data;
   generating, by the one or more processors, a gait feature corresponding to the current gait pattern based on a plurality of databases corresponding to a plurality of gait tasks;
   determining, by the one or more processors, a gait environment corresponding to the current gait pattern among the plurality of gait tasks based on the gait feature; and
   driving, by the one or more processors, the walking assistance apparatus based on the determined gait task and the sensed data.

14. A device configured to control a walking assistance apparatus, the device comprising:
   a memory configured to store computer-readable instructions; and
   one or more processors configured to execute the computer-readable instructions such that the one or more processors are configured to,
      receive sensed data from the walking assistance apparatus using a communication interface,
      generate a current gait pattern based on the sensed data,
      generate a gait feature corresponding the current gait pattern based a plurality of databases corresponding a plurality of gait tasks,
      determine a gait task corresponding to the current gait pattern among the plurality of gait tasks based on the gait feature, and
      control the walking assistance apparatus to drive based on the determined gait task and the sensed data.

15. The device of claim 14, wherein the one or more processors are further configured to output the determined gait task.

16. The device of claim 14, wherein the device is a wearable device or a mobile terminal.

17. A method, performed by a walking assistance system including an apparatus including one or more processors and a walking assistance apparatus, the method comprising:
   generating, by the walking assistance apparatus, sensed data by sensing gait motion of a user;
   receiving, by the one or more processors of the apparatus, sensed data from the walking assistance apparatus using a communication interface;
   generating, by the one or more processors of the apparatus, a current gait pattern based on the sensed data;
   generating, by the one or more processors of the apparatus, a gait feature corresponding the current gait pattern based a plurality of databases corresponding a plurality of gait tasks;

determining, by the one or more processors of the apparatus, a gait task corresponding to the current gait pattern among the plurality of gait tasks based on the gait feature; and controlling, by the one or more processors of the apparatus, the walking assistance apparatus to drive based on the determined gait task and the sensed data.

18. The method of claim 17, further comprising:
outputting the determined gait task.

19. The method of claim 17, wherein the apparatus is a wearable device or a mobile terminal.

20. A preprocessing apparatus configured to recognize a gait task and transmit a learning parameter for driving a walking assistance apparatus, the preprocessing apparatus comprising:
 a memory configured to store computer-readable instructions; and
 one or more processors configured to execute the computer-readable instructions such that the one or more processors are configured to,
  generate a plurality of gait patterns based on sensed data,
  classify the plurality of gait patterns based on a plurality of gait tasks,
  store the classified plurality of gait patterns as gait data in each of a plurality of databases corresponding to each of the plurality of gait tasks,
  generate a gait feature with respect to each of the plurality of gait patterns based on similarities among the plurality of gait patterns,
  generate a learning parameter with respect to a set learning model by applying the gait feature with respect to each of the gait data to the set learning model, and
  transmit the generated learning parameter to drive the walking assistance apparatus based on the generated learning parameter.

21. The preprocessing apparatus of claim 20, wherein the one or more processors are further configured to, determine similar gait patterns to each of the plurality of gait patterns from each of the plurality of databases, and
 generate the gait feature of each of the plurality of gait patterns based on similarities between each of the plurality of gait patterns and the determined similar gait patterns.

22. The preprocessing apparatus of claim 21, wherein the one or more processors are further configured to,
 calculate a mean value of the similarities between each of the plurality of gait patterns and the determined similar gait patterns, and
 generate a gait feature vector including a feature value corresponding to each of the plurality of gait tasks based on the mean value as an element.

23. The preprocessing apparatus of claim 22, wherein the one or more processors are configured to generate the gait feature by normalizing the gait feature vector with respect to each of the plurality of gait patterns.

24. The preprocessing apparatus of claim 20, wherein the one or more processors are further configured to,
 sense a heel strike indicating a state in which a sole of a user touches a ground from the sensed data, and
 detect the plurality of gait patterns based on a basic unit of a step including a single heel strike or a stride including two steps.

25. The preprocessing apparatus of claim 20, wherein the sensed data comprises at least one of acceleration data sensed by an inertial measurement unit (IMU) sensor, angular velocity data sensed by the IMU sensor, joint angle data sensed by a potentiometer, joint angular velocity data sensed by the potentiometer, or electromyography (EMG) data extracted from an EMG sensor.

26. The preprocessing apparatus of claim 20, wherein the one or more processors are further configured to normalize the plurality of gait patterns with respect to at least one of a time axis or a data axis.

27. The preprocessing apparatus of claim 20, wherein the one or more processors are further configured to store the classified plurality of gait patterns as the gait data in each of the plurality of databases using a k-d tree structure.

28. The preprocessing apparatus of claim 20, wherein the one or more processors are further configured to,
 map the gait feature with respect to each of the plurality of gait patterns to a feature space of a set dimension, and
 input the mapped gait feature into the set learning model.

* * * * *